United States Patent
Sim et al.

(10) Patent No.: US 8,648,089 B2
(45) Date of Patent: Feb. 11, 2014

(54) 1,3,6-SUBSTITUTED INDOLE DERIVATIVES HAVING INHIBITORY ACTIVITY FOR PROTEIN KINASE

(71) Applicant: Korea Institute of Science and Technology, Seoul (KR)

(72) Inventors: Tae Bo Sim, Seoul (KR); Young Jin Ham, Seoul (KR); Hwan Geun Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/684,507

(22) Filed: Nov. 24, 2012

(65) Prior Publication Data
US 2013/0079343 A1   Mar. 28, 2013

Related U.S. Application Data

(62) Division of application No. 12/858,114, filed on Aug. 17, 2010, now Pat. No. 8,329,708.

(30) Foreign Application Priority Data

Aug. 20, 2009   (KR) .......................... 10-2009-0077185

(51) Int. Cl.
  *A01N 43/54* (2006.01)
  *A61K 31/505* (2006.01)
(52) U.S. Cl.
  USPC ............................ 514/275; 514/273; 514/339
(58) Field of Classification Search
  USPC ................................. 544/180, 242; 546/268.1
  See application file for complete search history.

(56) References Cited

U.S. PATENT DOCUMENTS

2012/0271048 A1*  10/2012  Sim et al. ...................... 544/122

OTHER PUBLICATIONS

Webster's New World™ Medical Dictionary (Wiley Publishing, Inc. New York, NY) (http://www.credoreference.com/entry/webstermed/cancer).*
A.M. Traynor et al., Drugs of Today, 40(8), 697-710, 698 (2004).*
F.F. De Arruda, et al., Int. J. Radiation Oncology Biol. Phys., 64(2), 363-373 (2006).*
B.C. Bastian, Genetic Progression, in From Melanocytes to Melanoma the Progression to Malignancy 197, 201 (V. J. Hearing et al., eds., 2006.*
J. Tsai et al., 105 PNAS 3041-3046, 3041 (2008).*
S.K. Libutti, Colon Cancer in, 1 Cancer Principles & Practice of Oncology 1232, 1243 (V.T. DeVita, Jr. et al. eds., 8th ed., 2008).*
T. Carling et al., Thyroid Tumors in, 2 Cancer Principles & Practice of Oncology 1503 (V.T. DeVita, Jr. et al. eds., 8th ed., 2008).*
J. L. Raizer, Journal of Neuro-Oncology, 74(1), 77-86 (2005).*
R.G.W. Verhaak et al., Cancer Cell, 17(1), 1-24 (2010).*
L. Pusztai, Histopathologic and Molecular Markers of Prognosis and Response to Therapy, in Breast Cancer 324, 326-328 (Kelly k. Hunt et al., ed., 2nd ed., 2008).*
A. Kamb, Nature Reviews Drug Discovery 2, 161-165 (2005).*
.F. Smith, Molecular Cancer Therapeutics, 6, 428-440, 428 (2007).*
N.E. Sharpless et al., Nature Reviews Drug Discovery 5, 741-754, 742 (2006).*
Collins, Current Signal Transduction Therapy, 1, 13-23, 13 (2006).*
C. Abad-Zapatero, Drug Discovery Today, 1-8 (2010).*
Y. Song et al., Cancer a Conceptual Framework in, 1 Cancer Principles & Practice of Oncology 1, 5-6 (V.T. DeVita, Jr. et al. eds., 8th ed., 2008).*
B. Hann et al., Current Opinion in Cell Biology, 13, 778-784 (2001).*
K.P. Olive et al., Clinical Cancer Research 12, 5277-5287 (2006).*
A-M Bleau et al., 8 Cell Cycle 2937-2945 (2009).*
A. Scribner et al., 19 Bioorganic & Medicinal Chemistry Letters, 1517-1521 (2009).*
Peters, KG et al.: "Expression of Tie2/Tek in breast tumour vasculature provides a new marker for evaluation of tumour angiogenesis", *British Journal of Cancer*, 1998, 77(1), pp. 51-56.
Jones, Nina et al.: "Identification of Tek/Tie2 Binding Partners", *The Journal of Biological Chemistry*, vol. 274, No. 43, Issue of Oct. 22, 1999, pp. 30896-30905.
Lyons, Michael S. et al.: "Isolation of the Zebrafish Homologues for the *tie*-1 and *tie*-2 Endothelium-Specific Receptor Tyrosine Kinases", *Developmental Dynamics* 212, 1998, pp. 133-140.
Montagut, Clara et al.: "Elevated CRAF as a Potential Mechanism of Acquired Resistance to BRAF Inhibition in Melanoma", *Cancer Res* 2008; 68: (12), Jun. 15, 2008, pp. 4853-4861.
Tsai, James et al.: "Discovery of a selective inhibitor of oncogenic B-Raf kinase with potent antimelanoma activity", *PNAS*, Feb. 26, 2008, vol. 105, No. 8, pp. 3041-3046.
Wan, Paul T.C. et al.: "Mechanism of Activation of the RAF-ERK Signaling Pathway by Oncogenic Mutations of B-RAF", *Cell*, vol. 116, Mar. 19, 2004, pp. 855-867.
Rajagopalan, Harith et al.: "RAF/RAS oncogenes and mismatch-repair status", *Nature*, vol. 418, Aug. 29, 2002, p. 934.
Salvatore, Giuliana et al.: "Analysis of BRAF Point Mutation and RET/PTC Rearrangement Refines the Fine-Needle Aspiration Diagnosis of Papillary Thyroid Carcinoma", *Journal of Clinical Endocrinology & Metabolism*, 2004 89: pp. 5175-5180.
Tuveson, David A et al.: "BRAF as a potential therapeutic target in melanoma and other malignancies", *Cancer Cell*, Aug. 2003, vol. 4, pp. 95-98.
Davies, Helen et al.: "Mutations of the *BRAF* gene in human cancer", *Nature*, vol. 417, Jun. 27, 2002, pp. 949-954.

(Continued)

*Primary Examiner* — James O Wilson
*Assistant Examiner* — Alexander R Pagano
(74) *Attorney, Agent, or Firm* — Frommer Lawrence & Haug LLP; Ronald R Santucci

(57) ABSTRACT

Disclosed are a 1,3,6-substituted indole compound having inhibitory activity for protein kinases, a pharmaceutically acceptable thereof, and a pharmaceutical composition for prevention and treatment of diseases caused by abnormal cell growth including the compound as an active ingredient.
Since the novel indole compound exhibits superior inhibitory activity for various protein kinases involved in growth factor signal transduction, it is useful as an agent for preventing or treating cancers caused by abnormal cell growth.

3 Claims, 1 Drawing Sheet

(56) References Cited

OTHER PUBLICATIONS

Jaiswal, Rama K. et al.: "Nerve Growth Factor-mediated Activation of the Mitogen-activated Protein (MAP) Kinase Cascade Involves a Signaling Complex Containing B-Raf and HSP90", *The Journal of Biological Chemistry*, vol. 271, No. 39, Issue of Sep. 27, 1996, pp. 23626-23629.

Wellbrock, Claudia et al.: "The RAF Proteins Take Centre Stage", *Molecular Cell Biology*, vol. 5, Nov. 2004, pp. 875-885.

Tran, Nancy H. et al.: "B-Raf and Raf-1 Are Regulated by Distinct Autoregulatory Mechanism", *The Journal of Biological Chemistry*, vol. 280, No. 16, Issue of Apr. 22, 2005, pp. 16244-16253.

Yuryev, Anton et al.: "Isoform-Specific Localization of A-RAF in Mitochondria", *Molecular and Cellular Biology*, vol. 20, No. 13, Jul. 2000, pp. 4870-4878.

Caraglia, M. et al.: "Targeting Raf-kinase: molecular rationales and translational issues", *Annals of Oncology*, 17 (Supplement 7), Jun. 2006, pp. vii 124-vii 127.

Avruch, Joseph et al.: "Ras Activation of the Raf Kinase: Tyrosine Kinase Recruitment of the MAP Kinase Cascade", downloaded from rphr.endojournals.org by on Jul. 29, 2010, pp. 127-155.

Manning, G. et al.: "The Protein Kinase Complement of the Human Genome", *Science*, vol. 298, Dec. 6, 2002, pp. 1912-1934.

A. Scribner et al., 19 Biorganic & Medicinal Chemistry Letters, 1517-1521 (2009).

Selcukbiricik, F. et al.: "The role of K-RAS and B-RAF mutations as biomarkers in metastatic colorectal cancer," *Journal of BUON*, 2013, vol. 8, No. 1, pp. 116-123.

Saini, Kamal S. et al.: "Targeting the PI3K/AKT/mTOR and Raf/MEK/ERK pathways in the treatment of breast cancer," *Cancer Treatment Reviews*, May 6, 2013, http://dx.doi.org/10.1016/j.ctrv.2013.03.009.

Solus, Jason F. et al.: "Ras, Raf, and MAP Kinase in Melanoma," *Advances in Anatomic Pathology*, Jul. 2013, vol. 20, No. 4, pp. 217-226.

Zhao, Dongqiang et al.: "Rat kinase inhibitor protein inhibits esophageal cancer cell invasion through downregulation of matrix metalloproteinase expression," *Oncology Reports*, 2013, vol. 30, pp. 304-312.

Chiu, C-F et al.: "Raf activation by Ras and promotion of cellular metastasis require phosphorylation of prohibitin in the raft domain of the plasma membrane," *Oncogene*, Feb. 7, 2013, vol. 32, No. 6, pp. 777-787.

Bajusz, S. et al.: "Erfahrungen Über Das Verhalten Geschützter Peptide Bei Der Reaktion Mit Natrium in Flüssigem Ammoniak" ("Behavior of protected peptides on reaction with sodium in liquid ammonia"), *Peptides, Proceedings of the Fifth European Symposium, Oxford*, Sep. 1962, The Macmillan Company, New York, 1963, pp. 49-52.

Shimizu, Kenji et al.: "Molecular cloning of an activated human oncogene, homologous to v-*raf*, from primary stomach cancer," *Proceedings of the National Academy of Sciences of the United States of America*, Sep. 1985, vol. 82, pp. 5641-5645.

Wang, Jin et al.: "Immunohistochemical detection of the Raf kinase inhibitor protein in nonneoplastic gastric tissue and gastric cancer tissue," *Medical Oncology*, 2010, vol. 27, pp. 219-223.

Yan, Huang et al.: "Reduction of Raf Kinase Inhibitor Protein Expression is Associated with Lymph Node Metastasis in Resectable Non-small Cell Lung Cancer," 2012, *The Open Respiratory Medicine Journal*, vol. 6, pp. 135-138.

Leung, Thomas Ho-Yin et al.: "Deleted in liver cancer 2 suppresses cell growth via the regulation of the Raf-l-ERK1/2-p70S6K signalling pathway," *Liver International*, 2010, pp. 1315-1323.

Bläker, H. et al.: "Mutational Activation of the RAS-RAF-MAPK and the Wnt Pathway in Small Intestinal Adenocarcinomas," *Scandinavian Journal of Gastroenterology*, 2004, vol. 8, pp. 748-753.

Song, Shi-Peng et al.: "Reduced expression of Raf kinase inhibitor protein correlates with poor prognosis in pancreatic cancer," *Clinical and Translational Oncology*, 2012, vol. 14, pp. 848-852.

Gril, Brunilde et al.: "Pazopanib Reveals a Role for Tumor Cell B-Raf in the Prevention of HER2$^+$ Breast Cancer Brain Metastasis," *Clinical Cancer Research*, Jan. 1, 2011, vol. 17, No. 1, pp. 142-153.

Ikeda, Shogo et al.: "Amplification of Both c-*myc* and c-*raf* 1 Oncogenes in a Human Osteosarcoma," *Japanese Journal of Cancer Research*, Jan. 1989, vol. 80, pp. 6-9.

Finkelstein, Alexander, et al.: "Papillary thyroid carcinomas with and without *BRAF* V600E mutations are morphologically distinct," *Histopathology*, 2012, vol. 60, pp. 1052-1059.

McPhillips, Fiona et al.: "Raf-1 is the predominant Raf isoform that mediates growth factor-stimulated growth in ovarian cancer cells," *Carcinogenesis*, 2006, vol. 27, No. 4, pp. 729-739.

Arredondo, Juan et al.: "Receptor-mediated tobacco toxicity: cooperation of the Ras/Raf-1/MEK1/ERK and JAK-2/STAT-3 pathways downstream of $\alpha$7 nicotinic receptor in oral keratinocytes," *The FASEB Journal*, Oct. 2006, vol. 20, pp. 2093-2101.

Jin, Ning et al.: "Synergistic Action of a RAF Inhibitor and a Dual PI3K/mTOR Inhibitor in Thyroid Cancer," *Clinical Cancer Research*, Oct. 15, 2011, vol. 17, No. 20, pp. 6482-6489.

Salvatore, Giuliana et al: "Molecular profile of hyalinizing trabecular tumours of the thyroid: High prevalence of *RET/PTC* rearrangements and absence of *B-raf* and *N-ras* point mutations," *European Journal of Cancer*, 2005, vol. 41, pp. 816-821.

Banerjee, Pallavi et al.: "The Heme Oxygenase-1 Protein Is Overexpressed in Human Renal Cancer Cells following Activation of the Ras-Raf-ERK Pathway and Mediates Anti-Apoptotic Signal," *Journal of Biological Chemistry*, Sep. 23, 2011, vol. 286, No. 38, pp. 33580-33590.

Peng, Chang-Liang et al.: "Sorafenib induces growth inhibition and apoptosis in human synovial sarcoma cells via inhibiting the RAF/MEK/ERK signaling pathway," *Cancer Biology & Therapy*, Sep. 15, 2009, vol. 8, No. 18, pp. 1729-1736.

Wang, Jingqiang et al.: "B-Raf Activation Cooperates with PTEN Loss to Drive c-Myc Expression in Advanced Prostate Cancer," *Cancer Research*, Sep. 15, 2012, vol. 72, No. 18, pp. 4765-4776.

Zaravinos, Apostolos et al.: "implication of RAF and RKIP Genes in Urinary Bladder Cancer," *Pathology & Oncology Research*, 2011, vol. 17, pp. 181-190.

Tiacci, Enrico et al.: "Constant activation of the RAF-MEK-ERK pathway as a diagnostic and therapeutic target in hairy cell leukemia," *Haematologica*, 2013, vol. 98, No. 4, pp. 635-639.

Yosifov, Deyan Y. et al.: "Interleukin-6, osteopontin and Raf/MEK/ERK signaling modulate the sensitivity of human myeloma cells to alkylphosphocholines," *Leukemia Research*, 2012, vol. 36, pp. 764-772.

Jazirehi, Ali R. et al.: "Inhibition of the Raf-MEK1/2-ERK1/2 Signaling Pathway, Bcl-xL Down-Regulation, and Chemosensitization of Non-Hodgkin's Lymphoma B Cells by Rituximab," *Cancer Research*, 2004, vol. 64, pp. 7117-7126.

Li, Dan et al.: "Analysis of MiR-195 and MiR-497 Expression, Regulation and Role in Breast Cancer," *Clinical Cancer Research*, Apr. 1, 2011, vol. 17, No. 7, pp. 1722-1730.

* cited by examiner

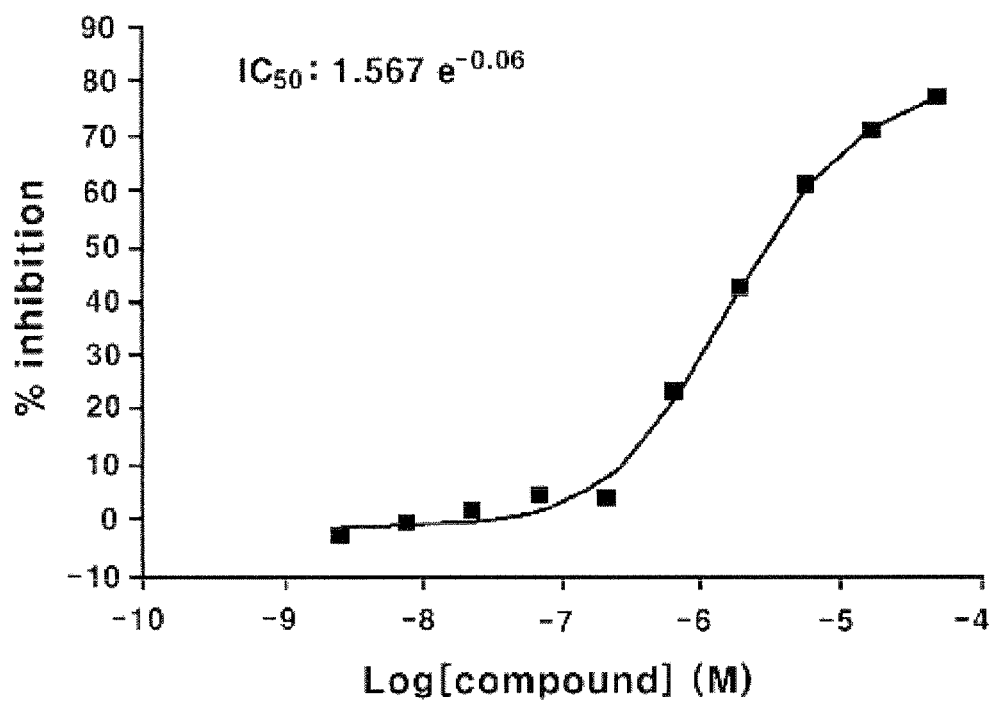

1,3,6-SUBSTITUTED INDOLE DERIVATIVES HAVING INHIBITORY ACTIVITY FOR PROTEIN KINASE

CROSS-REFERENCE TO RELATED APPLICATIONS

This application is a division of U.S. patent application Ser. No. 12/858,114 filed Aug. 17, 2010 which claims priority under 35 U.S.C. §119 to Korean Patent Application No. 10-2009-0077185, filed Aug. 20, 2009, in the Korean Intellectual Property Office, the disclosures of which are all incorporated herein by reference in their entirety.

TECHNICAL FIELD

The following disclosure relates to a 1,3,6-substituted indole compound having inhibitory activity for protein kinases, a pharmaceutically acceptable salts thereof, and a pharmaceutical composition for prevention and treatment of diseases caused by abnormal cell growth including the compound as an active ingredient.

BACKGROUND

A protein kinase is an enzyme which catalyzes phosphorylation of hydroxyl groups on tyrosine, serine and threonine residues of proteins. It plays an important role in signal transduction of growth factors involved in growth, differentiation and proliferation of cells.

For maintenance of homeostasis, it is essential that turning on and off of the signal transduction system be well balanced. However, mutation or overexpression of specific protein kinases disrupts the signal transduction system in normal cells (a state when in vivo signal transduction is continuously turned on) and causes various kinds of diseases including cancers, inflammations, metabolic diseases, brain diseases, or the like. Typical protein kinases that lead to diseases caused by abnormal cell growth include Raf, KDR, Fms, Tie2, SAPK2a, Ret, Abl, Abl(T315I), ALK, Aurora A, Bmx, CDK/cyclinE, Kit, Src, EGFR, EphA1, FGFR3, Flt3, Fms, IGF-1R, IKKb, IR, Itk, JAK2, KDR, Met, mTOR, PDGFRa, Plk1, Ret, Syk, Tie2, TrtB, and so forth.

Human genome is believed to contain 518 protein kinase genes and they constitute about 1.7% of all human genes [Manning et al. *Science*, 2002, 298, 1912]. Human protein kinases are largely divided into tyrosine-specific protein kinases (over 90 species) and serine/threonine-specific protein kinases. The tyrosine-specific protein kinases may be divided into 58 receptor tyrosine kinases, which are again grouped into 20 subfamilies, and 32 cytoplasmic/non-receptor tyrosine kinases, which are grouped into 10 subfamilies. The receptor tyrosine kinase has an extracellular domain capable of binding to a growth factor and a cytoplasmic active site that can phosphorylate the tyrosine residue. When a growth factor binds to the extracellular growth factor receptor site of the receptor tyrosine kinase, the receptor tyrosine kinase forms a dimer and the tyrosine residues in the cytoplasm are autophosphorylated. Then, the downstream proteins are sequentially phosphorylated, and as the signal transduction proceeds in the nucleus, the transcription factors that induce cancer are overexpressed in the end.

Raf is a serine/threonine (Ser/Thr)-specific protein kinase and serves the role of transmitting biological signals from activated growth factor receptors on the cell membrane into the nucleus. The mitogen-activated protein kinase (MAPK) signal transduction system is essential in cellular proliferation, division, survival, apoptosis, and the like. The MAPK signal transduction system largely consists of three kinase phosphorylation processes—i.e., sequential phosphorylation of MAPK kinase kinase (MAPKKK), MAPK kinase (MAPKK) and MAPK. Raf is a MAPKKK, MEK is a MAPKK, and the extracellular signal-regulated kinase (ERK) is a MAPK. When the receptor is activated, the small GTP-binding protein, Ras, is activated and the MAPK signal transduction into the nucleus is performed through sequential phosphorylation of Raf-MEK-ERK.

The Ras oncogene (especially k-Ras) in a permanently activated state is closely related to the onset of solid tumors such as pancreatic cancer (about 90%), rectal cancer (about 45%), liver cancer (about 30%), non-small cell lung cancer (about 35%), renal cancer (about 10%), or the like. If Raf-1 binds to activated Ras, serine 338 of Raf-1 is phosphorylated [Avruch, *J. Recent Progress in Hormone Research*, 2001, 56, 127], and the Raf-1 is activated. In contrast, if 14-3-3 protein binds to Raf-1 with phosphorylated serine 259, the Raf-1 is inactivated. The Raf kinase is also involved in the nuclear factor-κB (NF-κB) signal transduction system, which plays a key role in immune responses and inflammations [Caraglia, M. et al., *Annals of Oncology*, 2006, 17, 124]. That is, Raf phosphorylates inactivated IκB protein and induces migration of NF-κB protein into the nucleus, thereby stimulating a transcription factor that inhibits apoptosis.

Another apoptosis inhibition mechanism of Raf is as follows. Raf forms a dimer together with Bcl-2 and is translocated into the mitochondria. There, it phosphorylates Bad, thereby initiating apoptosis inhibition by Bcl-2. Accordingly, Raf is immunoprecipitated along with Bcl-2 [Yuryev, A. et al., *Mol. Cell. Biol.*, 2000, 20, 4870].

The three subtypes of Raf protein (A-Raf, B-Raf and C-Raf/Raf-1) have three conserved regions (CR1, CR2 and CR3) at the N-terminal regulatory domain and the C-terminal kinase domain. CR1 includes a Ras-binding domain (RBD) such as the cysteine-rich domain (CRD), CR2 includes a 14-3-3 protein-binding site (e.g., serine 259 of Raf-1), and CR3 includes a catalytic domain [Tran et al., *J. Biol. Chem.*, 2005, 280, 16244] and two activation segment phosphorylation sites (threonine 491 and serine 494 of Raf-1) [Wellbrock, C. *Nature Reviews Molecular Cell Biology*, 2004, 5, 875]. The three subtypes of Raf protein are expressed in different tissues. Whereas C-Raf is expressed in almost all tissues, A-Raf is mainly expressed in urogenital tissues (e.g., kidney, uterus and prostate gland) and B-Raf is mainly expressed in nervous, splenic and hematopoietic tissues [Jaiswal, R. K. et al., *J. Biol. Chem.*, 1966, 271, 23626].

Mutation of B-Raf is known to be associated with about 7% of all human cancers. Especially, it has been observed with high frequency (~70%) in melanoma, a type of skin cancer. Of the mutations of B-Raf, the B-Raf-V600E mutation, i.e., a point mutation with valine 600 of exon 15 being replaced by glutamic acid, mainly (about 90%) induce melanoma [Davies, H. et al., *Nature* 2002, 417, 949]. As compared with wild-type B-Raf, B-Raf-V600E has about 500 times higher in vitro kinase activity. Accordingly, B-Raf-V600E induces hyperactivation of the MAPK signal transduction and leads to cancer. The reason why B-Raf-V600E has such a high kinase activity is as follows. The glutamic acid 600 replaced by the point mutation mimics a phosphate group between the phosphorylation sites (threonine 598 and serine 601) located at the activation segment and, thereby, induces structural conformation of the permanently activated B-Raf kinase domain [Tuveson, D. A., *Cancer Cell*, 2003, 4, 95]. Up to the present, about 40 B-Raf mutations were found (mainly at the activation segment and the glycine-rich G-loop of the catalytic domain). However, occurrence of mutations other than V600E is fairly infrequent. In rectal cancer, about 10% of B-Raf mutations occur at the G-loop of the catalytic domain [Rajagopalan et al., *Nature* 2002 418, 934].

Although B-Raf has an auto-inhibition domain at the N-terminal, B-Raf becomes permanently activated when activated H-Ras binds thereto. This is caused by phosphorylation of serine 445. The phosphorylation of serine 338 of C-Raf corresponds to that of serine 445 of B-Raf. The B-Raf V600E mutation inhibits the auto-inhibition mechanism of B-Raf and turns it permanently activated.

The B-Raf-V600E mutation is observed at high frequency (about 50%) in papillary thyroid cancer [Salvatore, G. *J. Clin. Endocrinol. Metab.* 2004, 89, 5175]. Also, the B-Raf-V600E is closely associated with the onset of colon cancer (about 20%) and uterine cancer (about 30%).

Also, hyperactivation of C-Raf without oncogenic mutation is observed in renal carcinoma (about 50%) and hepatocellular carcinoma (HCC) (about 100%).

Sorafenib (RAY 43-9006, marketed as Nexavar) developed by Bayer and Onyx strongly inhibits C-Raf and both wild-type and mutant B-Raf. Further, sorafenib inhibits activity of the receptor tyrosine kinases, such as platelet-derived growth factor receptor, vascular endothelial growth factor receptors 1/2/3, fibroblast growth factor receptor, Flt-3, c-Kit, RET, or the like. It inhibits the kinase by stabilizing the DGF motif of the kinase domain to have an inactive conformation [Wan, P. T. et al., *Cell,* 2004, 116, 855]. Sorafenib was approved as a treatment for advanced renal cell carcinoma in 2005. The therapeutic effect of sorafenib on renal cancer originates from to the inhibition of vascular endothelial growth factor receptors 1/2/3 and other kinases rather than the inhibition of Raf. In the clinical trial phase II, a maximum allowed administration dose of sorafenib was 400 mg (twice a day). Administration of 600 mg (twice a day) of sorafenib may lead to grade 3 skin toxicity. Frequent adverse effects of sorafenib include hand-foot syndromes such as peeling of skin, rash and edema. In 2008, sorafenib was approved as a treatment for hepatocellular carcinoma. In addition, sorafenib showed therapeutic effect for intractable thyroid cancer, hormone-refractory prostate cancer and breast cancer in a clinical trial phase II. However, sorafenib shows no therapeutic effect on the skin cancer melanoma.

PLX4720, a 7-azaindole derivative developed by Plexxikon, induces apoptosis of melanoma cells such as 1205Lu (Raf-V660E overexpressed cells) [Tsai, J. et. al., *PNAS,* 2008, 105, 3041]. PLX4720 is a potent inhibitor of Raf-V660E kinase activity ($IC_{50}$=13 nM) and also inhibits the proliferation of A375 melanoma cells ($IC_{50}$=0.5 µM).

CHIR265 developed by Novartis and Chiron also strongly inhibits the kinase activity of B-Raf-V600E ($IC_{50}$=19 nM), KDR ($IC_{50}$=70 nM), PDGFR-b ($IC_{50}$=30 nM) and c-Kit ($IC_{50}$=20 nM). CHIR265 is currently in clinical trial phase I for melanoma patients.

Resistance to Raf inhibitors has been an emerging issue. Montagut et al. explained the mechanism of resistance to the Raf inhibitor by culturing M14 cells (human melanoma cells) with B-Raf-V600E mutation in the presence of a Raf inhibitor (AZ628) and acquiring clones resistant to the Raf inhibitor. Inhibition of B-Raf results in increased expression of C-Raf protein and decreased inhibitory effect on B-Raf-V600E. Meanwhile, the melanoma cells resistant to the Raf inhibitor (AZ628) exhibit increased susceptibility to the HSP90 inhibitor geldanamycin. Thus, inhibition of HSP90 may be a way to overcome the resistance to the Raf inhibitor [Montagut, C. *Cancer Research,* 2008, 68, 4853].

Vascular endothelial growth factor receptors (VEGFRs) are receptor tyrosine kinases (RTKs) and important regulatory factors of angiogenesis. They are involved in the formation of blood vessels and lymphatic vessels and in homeostasis, and exert important effects on nerve cell. Vascular endothelial growth factor (VEGF) is produced mostly by vascular endothelial cells, hematopoietic cells and stromal cells under a hypoxic condition or by stimulations from growth factors such as TGF, interleukin and PDGF. VEGF binds to VEGFR-1, -2 and -3. Each VEGF isoform binds to a specific receptor, thereby inducing the formation of a receptor homozygote or heterozygote, and activates the corresponding signal transduction system. The signal specificity of VEGFR is further fine-tuned by co-receptors such as neuropilin, heparan sulfate, integrin, cadherin, or the like.

The biological function of VEGF is mediated by type III RTK, VEGFR-1 (Flt-1), VEGFR-2 (KDR/Flk-1) and VEGFR-3 (Flt-4). VEGFR is closely related to Fms, Kit and PDGFR. Each VEGF binds to specific receptors. VEGF-A binds to VEGFR-1, -2 and receptor zygote, whereas VEGF-C binds to VEGFR-2, -3. PIGF and VEGF-B interact exclusively with VEGFR-1, and VEGF-E interacts only with VEGFR-2. VEGF-F interacts with VEGFR-1 or -2. Whereas VEGF-A, -B and PIGF are preferentially required for the formation of blood vessels, VEGF-C and -D are essential in the formation of lymphatic vessels. Angiogenesis is essential in the proliferation and transition of tumors, since it supplies nutrients and oxygen to the tumors and helps transition to cancer cells. Normally, angiogenesis is balanced by angiogenic stimulators and angiogenic inhibitors. If the balance is broken, as in cancer cells, the growth factor that affects the vascular endothelial cells most, i.e., VEGF, activates its receptor, VEGFR. At present, various researches are under way on the inhibitors that inhibit the receptor tyrosine kinase of VEGF using low-molecular-weight synthetic substances, which are advantageous in that they are applicable also to solid tumors and have fewer side effects because they inhibit angiogenesis in cancer cells only.

Tie2 is a kind of receptor tyrosine kinase which is deeply involved with angiogenesis and vasculature. The Tie2 domain structure is highly conserved in all vertebrates [Lyons et al., 1998]. The ligand of Tie2 is angiopoietin (Ang). Ang2 does not induce autophosphorylation of Tie2, but interferes with the activation of Tie2 by Ang1. In endothelial cells, the activation of Tie2 by Ang2 induces activation of PI3K-Akt [Jones et al., 1999]. In the mitogen-activated protein kinase (MAPK) signal transduction pathway, which is the main signal transduction system of Tie2, the adaptor protein GRB2 and the protein tyrosine phosphatase SHP2 play a key role in dimerization of the Tie2 receptor tyrosine kinase through autophosphorylation. Ang/Tie2 and the VEGF signal transduction pathway are important in angiogenesis of cancer cells. Tie2 is expressed in vascular endothelial cells. Especially, the expression increases remarkably at the site invaded by cancer cells. Overexpression of Tie2 was observed in breast cancer [Peters et al., 1998] and also in uterine cancer, liver cancer and brain cancer.

Several compounds with an indole structure have been synthesized. However, the indole compound of the present invention with specific substituents at the 1-, 3- and 6-positions of indole has never been synthesized. Thus, of course, the inhibitory activity against various protein kinases or the possibility as an agent for treatment and prevention of cancers of the 1,3,6-substituted indole compound has never been disclosed in any literature.

SUMMARY

The present invention relates to a novel 1,3,6-substituted indole compound having specific substituents at the 1-, 3- and 6-positions of indole or a pharmaceutically acceptable salt thereof.

The present invention also relates to a pharmaceutical composition for prevention and treatment of diseases caused by abnormal cell growth including the novel 1,3,6-substituted indole compound or a pharmaceutically acceptable thereof as an active ingredient.

In one general aspect, the present invention provides a 1,3,6-substituted indole compound represented by Chemical Formula, a pharmaceutically acceptable salt thereof, a hydrate thereof or a solvate thereof:

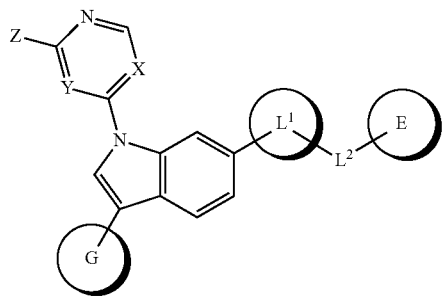

(1)

wherein

X and Y are independently selected from N or CH;

Z is selected from the group consisting of hydrogen; halogen; linear, branched or cyclic saturated or unsaturated $C_1$-$C_6$ alkyl; cyano; $OR^1$; —$SR^1$; $NHR^1$; —C(O)$NHR^1$; —NHC(O)$R^1$; —NHC(O)$NHR^1$; —S(O)$R^1$; and —S(O)$_2R^1$;

G is selected from the group consisting of halogen, 5- to 7-membered substituted or unsubstituted aryl, 5- to 7-membered substituted or unsubstituted heteroaryl containing 1 to 3 heteroatom(s) selected from nitrogen, oxygen and sulfur and a 5- to 7-membered substituted or unsubstituted heterocyclic group containing 1 to 3 heteroatom(s) selected from nitrogen, oxygen and sulfur;

$L^1$ is selected from the group consisting of 5- to 7-membered substituted or unsubstituted aryl, biaryl resulting from two fused 5- to 7-membered substituted or unsubstituted aryls, 5- to 7-membered substituted or unsubstituted heteroaryl containing 1 to 3 heteroatom(s) selected from nitrogen, oxygen and sulfur and a 5- to 7-membered substituted or unsubstituted heterocyclic group containing 1 to 3 heteroatom(s) selected from nitrogen, oxygen and sulfur;

$L^2$ is nonexistent or selected from the group consisting of —$NR^2$C(O)—, —C(O)$NR^2$—, —$NR^2$C(O)$NR^3$—, —S(O)$NR^2$— and —S(O)$_2NR^2$—;

E is selected from the group consisting of hydrogen; linear, branched or cyclic saturated or unsaturated $C_1$-$C_6$ alkyl; —$NO_2$; —$OR^3$; —$NR^3R^4$; —NHC(O)$R^3$; —C(O)$OR^3$; 5- to 7-membered substituted or unsubstituted aryl; biaryl resulting from two fused 5- to 7-membered substituted or unsubstituted aryls; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

$R^1$ is selected from the group consisting of hydrogen; linear, branched or cyclic saturated or unsaturated $C_1$-$C_6$ alkyl; saturated or unsaturated $C_1$-$C_6$ alkyl substituted with heteroaryl or heterocyclic ring selected from the group consisting of pyrrolidinonyl, pyrrolidinyl, piperidinyl, piperazinyl, morpholinyl and aziridinyl;

$R^2$, $R^3$ and $R^4$ are independently selected from the group consisting of hydrogen; and linear, branched or cyclic saturated or unsaturated $C_1$-$C_6$ alkyl;

wherein the above aryl, heteroaryl, biaryl or heterocyclic is independently substituted or unsubstituted with 1 to 3 substituent(s) selected from the group consisting of hydrogen; halogen; linear, branched or cyclic saturated or unsaturated $C_1$-$C_6$ alkyl; $C_1$-$C_6$ haloalkyl containing 1 to 10 halogen atoms; cyano; —$NO_2$; —OBoc; —$OR^5$; —O($CH_2$)$_n NR^6R^7$ (where n is an integer from 1 to 6); —$NR^6R^7$; —$NR^5COR^6$; —$NR^5$C(O)$NR^6R^7$; —C(O)$R^6$; —C(O)$OR^6$; —C(O)$NR^6R^7$; —C(O)NH($CH_2$)$_n NR^6R^7$; —S(O)$R^6$; —S(O)$_2R^6$; —S(O)$_2NR^6R^7$, 5- to 7-membered aryl, biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; and $R^5$, $R^6$ and $R^7$ are independently selected from the group consisting of hydrogen; halogen; linear, branched or cyclic saturated or unsaturated $C_1$-$C_6$ alkyl; 5- to 7-membered aryl; biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; or $NR^6R^7$ forms 5- to 7-membered heteroaryl or a heterocyclic ring by further including 1 to 3 other heteroatom(s), wherein the aryl, biaryl, heteroaryl or heterocyclic ring may be substituted with 1 to 3 substituent(s) selected from the group consisting of halogen, $C_1$-$C_6$ alkyl and $C_1$-$C_6$ haloalkyl containing 1 to 10 halogen atoms.

The 1,3,6-substituted indole compound represented by Chemical Formula 1, a pharmaceutically acceptable salt thereof, a hydrate thereof or a solvate thereof has superior capability of inhibiting the activity of protein kinases selected from Raf, KDR, Fms, Tie2, SAPK2a, Ret, Abl, Abl(T315I), ALK, Aurora A, Bmx, CDK/cyclinE, Kit, Src, EGFR, EphA1, FGFR3, Flt3, Fms, IGF-IR, IKKb, IR, Itk, JAK2, KDR, Met, mTOR, PDGFRa, Plk1, Ret, Syk, Tie2 and TrtB, and thus is effective for preventing and treating diseases caused by abnormal cell growth.

The diseases caused by abnormal cell growth that may be prevented or treated by the compound according to the present invention may include various cancers selected from stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, or the like.

Other features and aspects will be apparent from the following detailed description, the drawings, and the claims.

BRIEF DESCRIPTION OF THE DRAWING

The above and other objects, features and advantages of the present invention will become apparent from the following description of preferred embodiments given in conjunction with the accompanying drawing, in which:

FIG. 1 shows an inhibitory activity of 1-(2-methoxyphenyl)-3-(3-(3-(4-methoxyphenyl)-1-(6-(methylamino)pyrimidin-4-yl)-1H-indol-6-yl)phenyl)urea (compound of Example 39) for B-Raf-V600E kinase.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a", an and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawing.

A pharmaceutically acceptable salt of the 1,3,6-substituted indole compound represented by Chemical Formula 1 may be prepared by a method commonly employed in the art. A pharmaceutically acceptable salt should be less toxic to the human body and should not have negative effects on the biological activity and physical and chemical properties of the mother compound. The pharmaceutically acceptable salt includes a free acid, an acid addition salt of a base compound represented by Chemical Formula 1, an alkali metal salt (e.g., a sodium salt), an alkaline earth metal salt (e.g., a calcium salt), an organic salt, an organic base addition salt of a carboxylic acid represented by Chemical Formula 1, and an amino acid addition salt. The free acid that may be used to prepare the pharmaceutically acceptable salt includes an inorganic acid or an organic acid. The inorganic acid may be hydrochloric acid, sulfuric acid, nitric acid, phosphoric acid, perchloric acid, bromic acid, or the like. The organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, or the like. The organic base that may be used to prepare the organic base addition salt includes tris(hydroxymethyl)methylamine, dicyclohexylamine, or the like. The amino acid that may be used to prepare the amino acid addition salt includes a naturally occurring amino acid such as alanine, glycine, or the like.

The 1,3,6-substituted indole compound represented by Chemical Formula 1 includes, in addition to the pharmaceutically acceptable salts, all hydrates and solvates. The hydrate or the solvate may be prepared by dissolving the 1,3,6-substituted indole compound represented by Chemical Formula 1 in a water-miscible solvent such as methanol, ethanol, acetone and 1,4-dioxane, adding a free acid or a free base thereto, and then performing crystallization or recrystallization. In that case, a solvate (particularly a hydrate) may be formed. Accordingly, the compound of the present invention includes, in addition to the compounds containing various amounts of water that can be prepared through, for example, lyophilization, stoichiometric solvates including hydrates.

Hereunder is given a detailed description about the substituents used to define the compound according to the present invention.

In the present invention, 'halogen' means a fluorine, chlorine, bromine or iodine atom.

In the present invention, 'alkyl' means a $C_1$-$C_6$ aliphatic saturated hydrocarbon group, including methyl, ethyl, n-propyl, i-propyl, cyclopropyl, n-butyl, i-butyl, t-butyl, cyclobutyl, cyclopropylmethyl, n-pentyl, i-pentyl, neopentyl, t-pentyl, cyclopentyl, cyclobutylmethyl, n-hexyl, i-hexyl, cyclohexyl, cyclopentylmethyl, heptyl, cyclohexylmethyl, octyl, or the like.

In the present invention, 'haloalkyl' means an alkyl group with one or more hydrogen(s) substituted by halogen atom(s), such as trifluoromethyl.

In the present invention, 'alkoxy' means a hydroxyl group with the hydrogen substituted by $C_1$-$C_6$ alkyl group including methoxy, ethoxy, n-propoxy, i-propoxy, n-butoxy, i-butoxy and t-butoxy.

In the present invention, 'aryl' means a mono-, bi- or tricyclic aromatic hydrocarbon group, such as phenyl, naphthyl, anthracenyl, phenanthrenyl, or the like.

In the present invention, 'biaryl' means an aromatic hydrocarbon group formed from two fused aryl groups, such as biphenyl, phenoxyphenyl, benzoylphenyl, phenyldiazenylphenyl, or the like.

In the present invention, 'heteroaryl' means a mono-, bi- or tricyclic aromatic heterohydrocarbon group containing one or more heteroatom(s), such as pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrazinyl, pyridazinyl, pyrimidinyl, triazolyl, indolyl, isoindolyl, benzofuranyl, benzofurazanyl, dibenzofuranyl, isobenzofuranyl, indazolyl, benzimidazolyl, benzoxazolyl, benzisoxazolyl, benzothiazolyl, dibenzothiophenyl, naphthyridyl, benzisothiazolyl, quinolinyl, isoquinolinyl, quinoxalinyl, phthalazinyl, cinnolinyl, quinazolinyl, or the like.

In the present invention, 'heterocyclic ring' means a heterohydrocarbon ring containing one or more heteroatom(s), such as morpholinyl, piperidinyl, piperazinyl, N-protected piperazinyl, or the like.

Preferably, in the 1,3,6-substituted indole compound represented by Chemical Formula 1, X and Y are independently selected from N or CH; Z is selected from the group consisting of hydrogen, halogen, —$SR^1$, $NHR^1$ and —$S(O)R^1$; G is selected from the group consisting of halogen, indolyl. and substituted or unsubstituted aryl; $L^1$ is selected from the group consisting of substituted or unsubstituted aryl, and a substituted or unsubstituted heterocyclic ring containing 1 to 3 heteroatom(s) selected from nitrogen, oxygen and sulfur; $L^2$ is nonexistent or selected from the group consisting of —$NR^2C(O)$— and —$NR^2C(O)NR^3$—; E is selected from the group consisting of hydrogen, linear-, branched- or cyclic saturated or unsaturated $C_1$-$C_6$ alkyl, —$NO_2$, —$OR^3$, —$NR^3R^4$, —$NHC(O)R^3$ and substituted or unsubstituted aryl; $R^1$, $R^2$, $R^3$ and $R^4$ are independently selected from the group consisting of hydrogen, linear-, branched- or cyclic saturated or unsaturated $C_1$-$C_6$ alkyl and substituted or unsubstituted aryl; the substituted aryl or heterocyclic ring is independently aryl or a heterocyclic ring substituted with 1 to 3 substituent(s) selected from the group consisting of halogen, linear, branched or cyclic saturated or unsaturated $C_1$-$C_6$ alkyl, $C_1$-$C_6$ haloalkyl containing 1 to 10 halogen atoms, cyano, —$NO_2$, —OBoc, —$OR^5$, —$O(CH_2)_n NR^6 R^7$ (where n is an integer from 1 to 6), —$NR^6 R^7$, —$NR^5 COR^6$, —$NR^5 C(O)NR^6 R^7$, —$C(O)R^6$, —$C(O)OR^6$, —$C(O)NR^6 R^7$, —$C(O)NH(CH_2)_n NR^6 R^7$, substituted or unsubstituted aryl and a heterocyclic ring containing 1 to 3 heteroatom(s) selected from nitrogen, oxygen and sulfur; $R^5$, $R^6$ and $R^7$ are independently selected from the group consisting of hydrogen, halogen, linear, branched or cyclic saturated or unsaturated $C_1$-$C_6$ alkyl and substituted or unsubstituted aryl, or $NR^6 R^7$ forms a heterocyclic ring by optionally further including 1 to 3 other heteroatom(s), wherein the aryl or heterocyclic ring may be substituted with 1 to 3 substituent(s) selected from the group consisting of halogen, $C_1$-$C_6$ alkyl and $C_1$-$C_6$ haloalkyl containing 1 to 10 halogen atoms; the aryl is phenyl; and the heterocyclic ring is selected from the group consisting of morpholinyl, piperidinyl, piperazinyl and N-protected piperazinyl.

More preferably, in the 1,3,6-substituted indole compound represented by Chemical Formula 1, X and Y are independently N or CH; Z is hydrogen, Cl, —$SCH_3$, $NH_2$, $NHCH_3$, NH-cyclopropyl, $NHCH_2CH_2$-morpholinyl or —$S(O)CH_3$; G is Br, indolyl or substituted or unsubstituted phenyl; $L^1$ is substituted or unsubstituted phenyl, piperazinyl or N-Boc-piperazinyl; $L^2$ is nonexistent or —NHC(O)— or —NHC(O)NH—; E is hydrogen, cyclohexyl, —$NO_2$, —OH, —$OCH_3$, —$NH_2$, —$NHC(O)CH_3$ or substituted or unsubstituted phenyl; and the substituted phenyl is phenyl substituted with 1 to 3 substituent(s) selected from the group consisting of —Cl, —F, —$CH_3$, —$CF_3$, —CN, —$NO_2$, —OH, —OBoc, —$OCH_3$, —$OCH_2CH_2N(CH_3)_2$, —$NH_2$, —$NHC(O)CH_3$, —NHC(O)Ph, —NHC(O)-Ph(4-Cl,3-$CF_3$), $NHSO_2$-cyclopropyl, —C(O)OH, —$C(O)OCH_2CH_3$, —C(O)NH-cyclopropyl, —$C(O)NHCH_2CH_2$-morpholinyl, morpholinyl, 4-ethylpiperazinyl and 4-methylimidazolyl.

Specific examples of the 1,3,6-substituted indole compound represented by Chemical Formula 1 include:

tert-butyl 4-(3-bromo-1-(pyridin-4-yl)-1H-indol-6-yl)piperazine-1-carboxylate;
4-(3-bromo-1-(pyridin-4-yl)-1H-indol-6-yl)phenol;
3-bromo-6-(3-nitrophenyl)-1-(pyridin-4-yl)-1H-indole;
3-bromo-1-(2-(methylthio)pyrimidin-4-yl)-6-(3-nitrophenyl)-1H-indole;
3-bromo-1-(6-chloropyrimidin-4-yl)-6-(3-nitrophenyl)-1H-indole;
6-(3-bromo-6-(3-nitrophenyl)-1H-indol-1-yl)-N-methylpyrimidin-4-amine;
3-bromo-1-(6-chloropyrimidin-4-yl)-6-(4-methoxyphenyl)-1H-indole;
6-(3-bromo-6-(4-methoxyphenyl)-1H-indol-1-yl)-N-methylpyrimidin-4-amine;
tert-butyl 4-(3-(4-methoxyphenyl)-1-(pyridin 4-yl)-1H-indol-6-yl)piperazine-1-carboxylate;
3-(4-methoxyphenyl)-6-(piperazin-1-yl)-1-(pyridin-4-yl)-1H-indole;
4-(6-(piperazin-1-yl)-1-(pyridin-4-yl)-1H-indol-3-yl)phenol;
tert-butyl 4-(3-(4-(tert-butoxycarbonyloxy)phenyl)-1-(pyridin-4-yl)-1H-indol-6-yl)piperazine-1-carboxylate;
tert-butyl 4-(3-(4-hydroxyphenyl)-1-(pyridin-4-yl)-1H-indol-6-yl)piperazine-1-carboxylate;
tert-butyl 4-(3-(4-(2-(dimethylamino)ethoxy)phenyl)-1-(pyridin-4-yl)-1H-indol-6-yl)piperazine-1-carboxylate;
N,N-dimethyl-2-(4-(6-(piperazin-1-yl)-1-(pyridin-4-yl)-1H-indol-3-yl)phenoxy)ethanamine;
3-(4-methoxyphenyl)-6-(3-nitrophenyl)-1-(pyridin-4-yl)-1H-indole;
4-(6-(3-nitrophenyl)-1-(pyridin-4-yl)-1H-indol-1-yl)phenol;
4-(6-(3-aminophenyl)-1-(pyridin-4-yl)-1H-indol-3-yl)phenol;
N,N-dimethyl-2-(4-(6-(3-nitrophenyl)-1-(pyridin-4-yl)-1H-Indol-3-yl)phenoxy)ethanamine;
3-(3-(4-(2-(dimethylamino)ethoxy)phenyl)-1-(pyridin-4-yl)-1H-indol-6-yl)benzenamine;
N-(3-(3-(4-(2-(dimethylamino)ethoxy)phenyl)-1-(pyridin-4-yl)-1H-indol-6-yl)phenyl)acetamide;
6-(6-(4-methoxyphenyl)-3-(3-nitrophenyl)-1H-indol-1-yl)-N-methylpyrimidin-4-amine;
6-(3-(1-aminophenyl)-6-(4-methoxyphenyl)-1H-Indol-1-yl)-N-methylpyrimidin-4-amine;
N-(3-(6-(4-ethoxyphenyl)-1-(6-(methylamino)pyrimidin-4-yl)-1H-indol-3-yl)phenyl)acetamide;
ethyl 4-(6-(4-methoxyphenyl)-1-(6-(methylamino)pyrimidin-4-yl)-1H-indol-3-yl)benzoate;
4-(6-(4-methoxyphenyl)-1-(6-(methylamino)pyrimidin-4-yl)-1H-indol-3-yl)benzoate;
4-(6-(4-methoxyphenyl)-1-(6-(methylamino)pyrimidin-4-yl)-1H-indol-3-yl)-N-(2-morpholinoethyl)benzamide;
3-(4-methoxyphenyl)-1-(2-(methylthio)pyrimidin-4-yl)-6-(3-nitrophenyl)-1H-indole;
3-(4-methoxyphenyl)-1-(2-(methylsulfinyl)pyrimidin-4-yl)-6-(3-nitrophenyl)-1H-indole;
4-(3-(4-methoxyphenyl)-6-(3-nitrophenyl)-1H-indol-1-yl)pyrimidin-2-amine;
6-(3-(4-methoxyphenyl)-6-(3-nitrophenyl)-1H-indol-1-yl)-N-methylpyrimidin-4-amine;
6-(3-(3-aminophenyl)-3-(4-methoxyphenyl)-1H-indol-1-yl)-N-methylpyrimidin-4-amine;
1-(4-chloro-3-(trifluoromethyl)phenyl)-3-(3-(3-(4-methoxyphenyl)-1-(6-(methylamino)pyrimidin-4-yl)-1H-indol-6-yl)phenyl)urea;
1-(3,4-dichlorophenyl)-3-(3-(3-(4-methoxyphenyl)-1-(6-(methylamino)pyrimidin-4-yl)-1H-indol-6-yl)phenyl)urea;
1-(2-methoxyphenyl)-3-(3-(3-(4-methoxyphenyl)-1-(6-(methylamino)pyrimidin-4-yl)-1H-indol-6-yl)phenyl)urea;
1-(2-fluorophenyl)-3-(3-(3-(4-methoxyphenyl)-1-(6-(methylamino)pyrimidin-4-yl)-1H-indol-6-yl)phenyl)urea;
1-cyclohexyl-3-(3-(3-(4-methoxyphenyl)-1-(6-(methylamino)pyrimidin-4-yl)-1H-indol-6-yl)phenyl)urea;
N-(3-(3-(4-methoxyphenyl)-1-(6-(methylamino)pyrimidin-4-yl)-1H-indol-6-yl)phenyl)-4-methyl-3-nitrobenzamide;
N-(3-(3-(4-methoxyphenyl)-1-(6-(methylamino)pyrimidin-4-yl)-1H-indol-6-yl)phenyl)-3-morpholino-5-(trifluoromethyl)benzamide;
N-(3-(3-(4-methoxyphenyl)-1-(6-(methylamino)pyrimidin-4-yl)-1H-indol-6-yl)phenyl)-3-(4-methyl-1H-imidazol-1-yl)-5-(trifluoromethyl)benzamide;
1-(4-chloro-3-(trifluoromethyl)phenyl)-3-(3-(6-(4-methoxyphenyl)-1-(6-(methylamino)pyrimidin-4-yl)-1H-indol-3-yl)phenyl)urea;
4-chloro-N-(3-(6-(4-methoxyphenyl)-1-(6-(methylamino)pyrimidin-4-yl)-1H-indol-3-yl)phenyl)-3-(trifluoromethyl)benzamide;
N-cyclopropyl-4-(6-(4-methoxyphenyl)-1-(6-(methylamino)pyrimidin-4-yl)-1H-indol-3-yl)benzamide;
1-(2,6-dimethylphenyl)-3-(3-(3-(4-methoxyphenyl)-1-(6-(methylamino)pyrimidin-4-yl)-1H-indo)-6-yl)phenyl)urea;

1-(4-(4-ethylpiperazin-1-yl)-2-methoxyphenyl)-3-(3-(3-(4-methoxyphenyl)-1-(6-(methyl amino)pyrimidin-4-yl)-1H-indol-6-yl)phenyl)urea;

1-(5-chloro-2,4-dimethoxyphenyl)-3-(3-(3-(4-methoxyphenyl)-1-(6-(methylamino)pyrimidin-4-yl)-1H-indol-6-yl)phenyl)urea;

N-(3-(6-(4-methoxyphenyl)-1-(6-(methylamino)pyrimidin-4-yl)-1H-indol-3-yl)phenyl)cyclopropanecarboxamide;

N-(3-(6-(4-methoxyphenyl)-1-(6-(methylamino)pyrimidin-4-yl)-1H-indol-3-yl)phenyl)cyclopropanesulfonamide;

6-(6-(4-methoxyphenyl)-1H, 1'H-3,6'-biindol-1-yl)-N-methylpyrimidin-4-amine;

6-(6-(4-methoxyphenyl)-3-(4-nitrophenyl)-1H-indol-1-yl)-N-methylpyrimidin-4-amine;

6-(3-(4-aminophenyl)-6-(4-methoxyphenyl)-1H-indol-1-yl)-N-methylpyrimidin-4-amine;

6-(3-bromo-6-(4-methoxyphenyl)-1H-indol-1-yl)-N-(2-morpholinoethyl)pyrimidin-4-amine;

6-(3-bromo-6-(4-methoxyphenyl)-1H-indol-1-yl)-N-cyclopropylpyrimidin-4-amine;

6-(6-(4-methoxyphenyl)-3-(3-nitrophenyl)-1H-indol-1-yl)-N-(2-morpholinoethyl)pyrimidin-4-amine;

N-cyclopropyl-6-(6-(4-methoxyphenyl)-3-(3-nitrophenyl)-1H-indol-1-yl)pyrimidin-4-amine;

6-(3-(3-aminophenyl)-6-(4-methoxyphenyl)-1H-indol-1-yl)-N-(2-morpholinoethyl)pyrimidin-4-amine;

6-(3-(3-aminophenyl)-6-(4-methoxyphenyl)-1H-indol-1-yl)-N-cyclopropylpyrimidin-4-amine; and ethyl 4-(6-(4-methoxyphenyl)-1-(6-(2-morpholinoethylamino)pyrimidin-4-yl)-1H-indol-3-yl)benzoate.

The present invention also provides a method for preparing the indole compound represented by Chemical Formula 1. A typical example is as follows.

According to Scheme 1, a Suzuki coupling reaction of a bromine compound represented by Chemical Formula 2 with a boronic acid compound represented by Chemical Formula 3 is performed using an organometallic compound to prepare the 3,6-substituted indole compound represented by Chemical Formula 1.

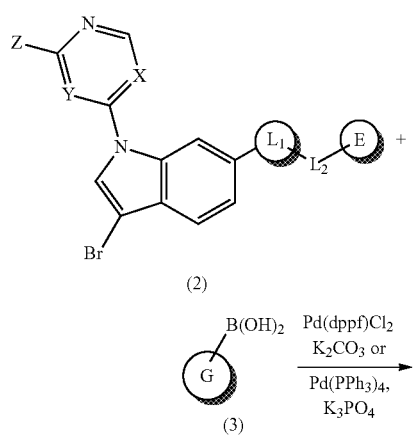

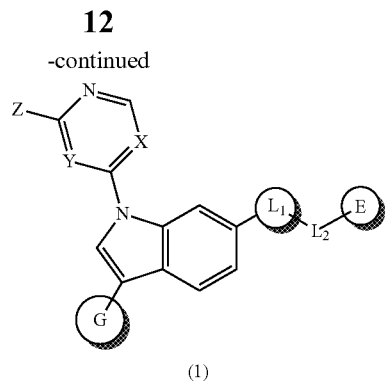

In Scheme 1, X, Y, Z, $L_1$, $L_2$, E and G are the same as defined above.

Schemes 2 to 4 exemplify introduction of various substituents to the 1,3,6-substituted indole compound represented by Chemical Formula 1.

According to Scheme 2, various $OR^2$ groups are introduced to the substituent G at the C-3 position of indole. It is performed by a two step process. First, a methoxy compound represented by Chemical Formula 1a is deprotected to prepare an alcohol compound represented by Chemical Formula 1b (Step 2-1). Then, the alcohol compound represented by Chemical Formula 1b is reacted with a compound represented by Chemical Formula 10 under a basic condition to prepare an $OR^5$-substituted compound represented by Chemical Formula 1c (Step 2-2).

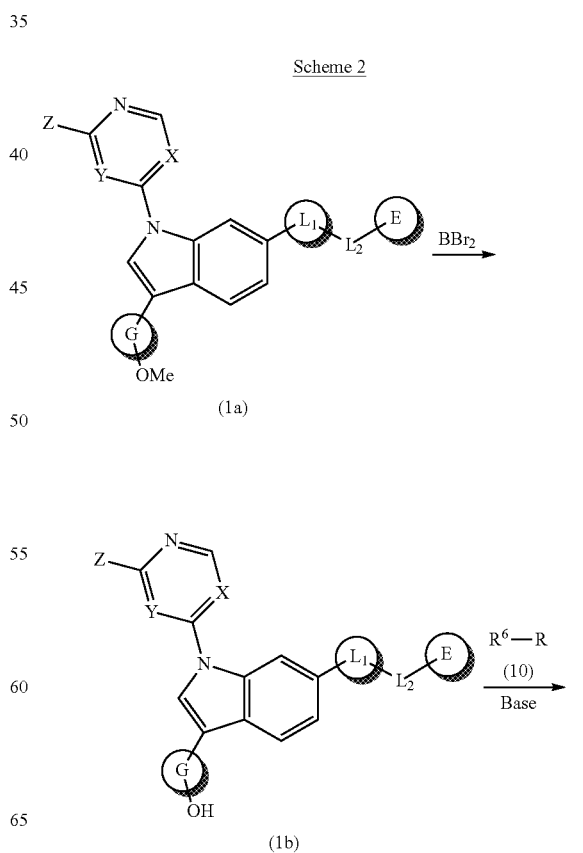

-continued

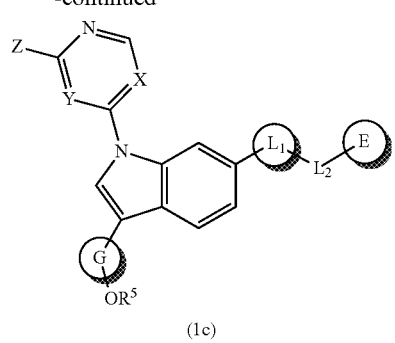

(1c)

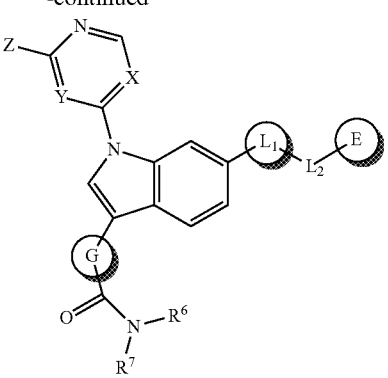

(1f)

In Scheme 2, X, Y, Z, $L_1$, $L_2$, E and G are the same as defined above, R is halogen or a leaving group, and the base is sodium tert-butoxide, sodium hydride, or the like.

According to Scheme 3, various amide groups represented by —$CONR^6R^7$ are introduced to the substituent G at the C-3 position of indole. It is performed by a two step process. First, a carboxylate ester compound represented by Chemical Formula id is hydrolyzed to prepare a carboxylic acid compound represented by Chemical Formula 1e (Step 3-1). Then, the carboxylic acid compound represented by Chemical Formula 1e is coupled with an amine compound represented by Chemical Formula 11 to prepare an amide compound represented by Chemical Formula 1f (Step 3-2).

In Scheme 3, X, Y, Z, $L_1$, $L_2$, E, G, $R^6$ and $R^7$ are the same as defined above.

According to Scheme 4, various amide groups represented by —$NR^5COR^6$ are introduced to the substituent G at the C-3 position of indole. It is performed by a two step process. First, a nitro compound represented by Chemical Formula 1g is reduced to prepare an amine compound represented by Chemical Formula 1h (Step 4-1). Then, the amine compound represented by Chemical Formula 1h is coupled with an acyl compound represented by Chemical Formula 12 to prepare an amide compound represented by Chemical Formula 1i (Step 4-2).

Scheme 3

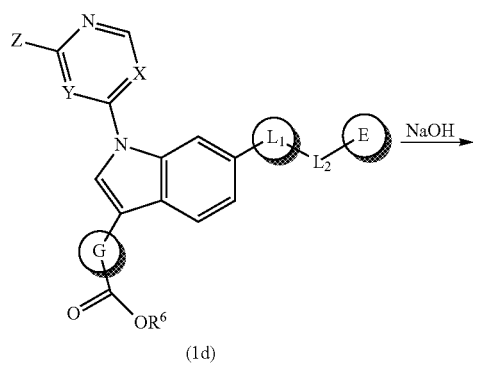

(1d)

Scheme 4

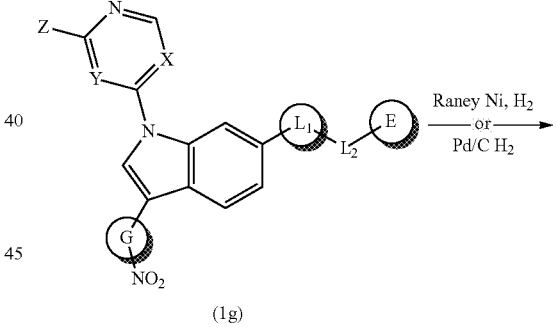

(1g)

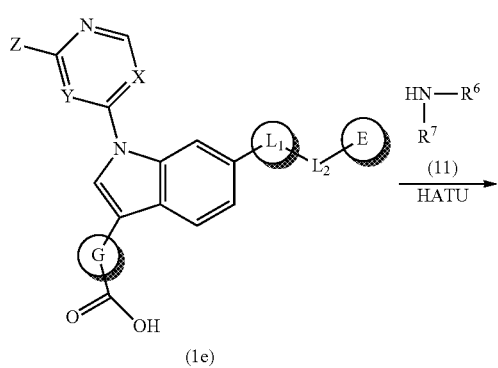

(1e)

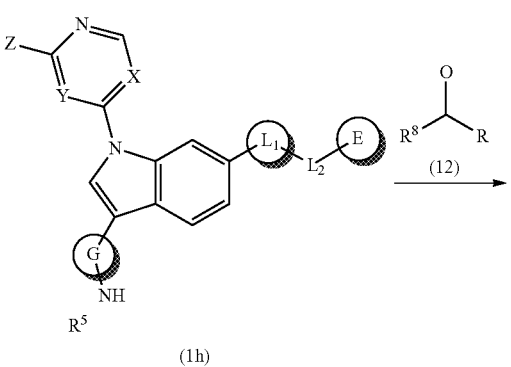

(1h)

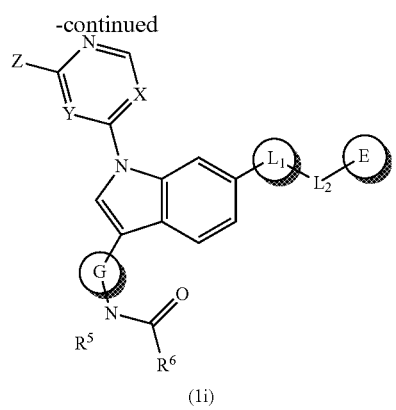

In Scheme 4, X, Y, Z, $L_1$, $L_2$, E, G, $R^5$ and $R^6$ are the same as defined above, and R is halogen or a leaving group.

According to Scheme 5, various -$L^2$-E groups are introduced to the substituent $L^1$ at the C-6 position of indole. It is performed by a two step process. First, a nitro compound represented by Chemical Formula 1j is reduced to prepare an amine compound represented by Chemical Formula 1k (Step 5-1). Then, the amine compound represented by Chemical Formula 1k is coupled with an isocyanate compound represented by Chemical Formula 13 or a carboxylic acid compound represented by Chemical Formula 14 to prepare a compound represented by Chemical Formula 1 (Step 5-2).

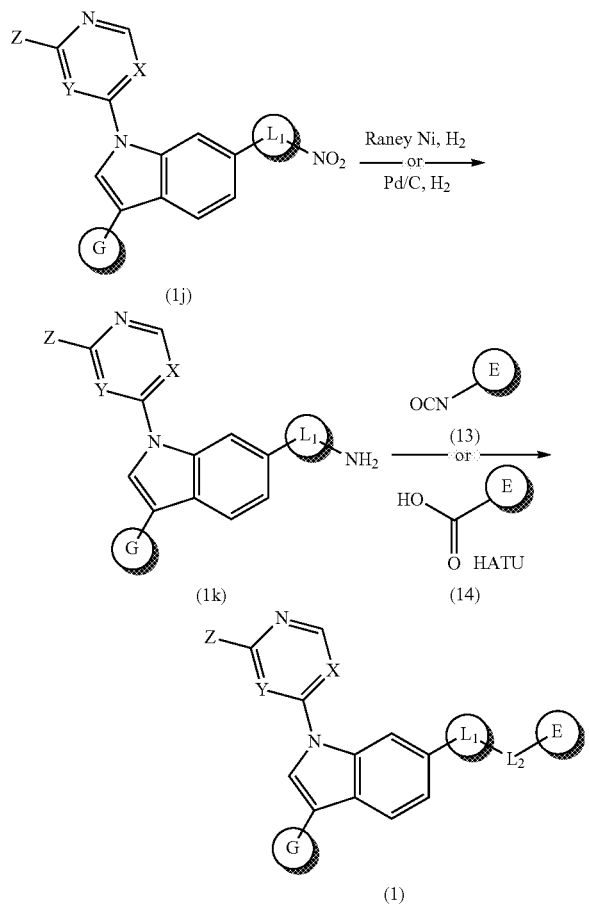

In Scheme 5, X, Y, Z, $L_1$, $L_2$, E and G are the same as defined above.

The compound represented by Chemical Formula 2, which is used as a starting material in Scheme 1, may be prepared by Scheme 6 or 7.

According to Scheme 6, a 6-bromoindole compound represented by Chemical Formula 3 is Suzuki-coupled using an organometallic compound to prepare a 6-substituted indole compound represented by Chemical Formula 4 (Step 6-1). Then, the 6-substituted indole compound represented by Chemical Formula 4 is coupled with a compound represented by Chemical Formula 8 using a metal comprising palladium to prepare a compound represented by Chemical Formula 5a (Step 6-2). Then, the compound represented by Chemical Formula 5a is brominated to prepare the bromine compound represented by Chemical Formula 2 (Step 6-3).

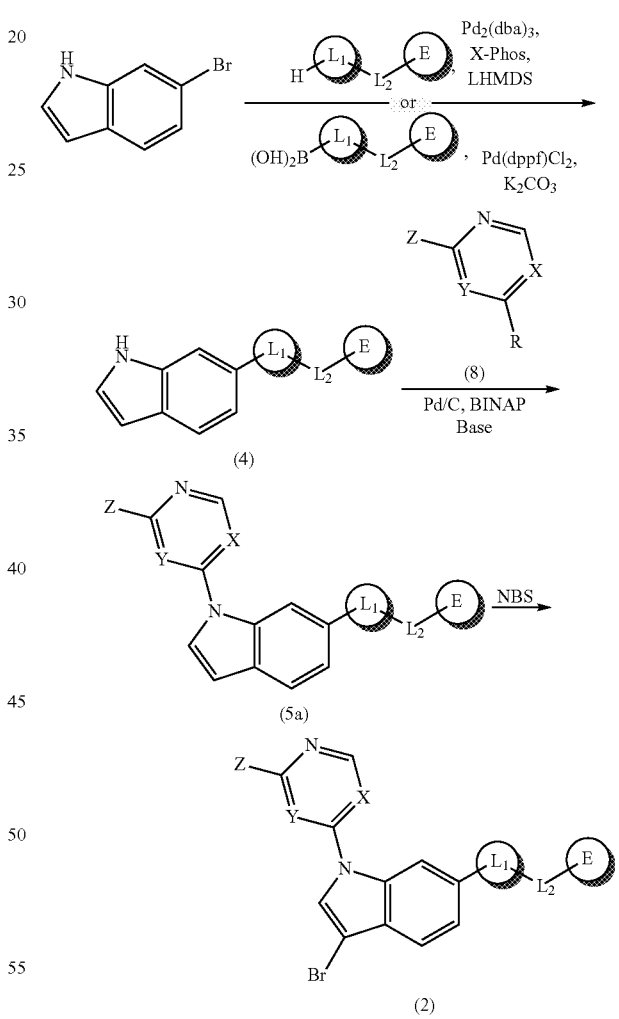

In Scheme 6, X, Y, Z, $L_1$, $L_2$ and E are the same as defined above, R is halogen or a leaving group, and the base is sodium tert-butoxide, sodium hydride, or the like.

According to Scheme 7, a 6-bromoindole compound represented by Chemical Formula 3 is Suzuki-coupled using an organometallic compound to prepare a 6-substituted indole compound represented by Chemical Formula 4 (Step 7-1). Then, the 6-substituted indole compound represented by Chemical Formula 4 is brominated to prepare a compound represented by Chemical Formula 5b (Step 7-2). Then, the compound represented by Chemical Formula 5b is coupled with a compound represented by Chemical Formula 8 using a base to prepare the bromine compound represented by Chemical Formula 2 (Step 7-3).

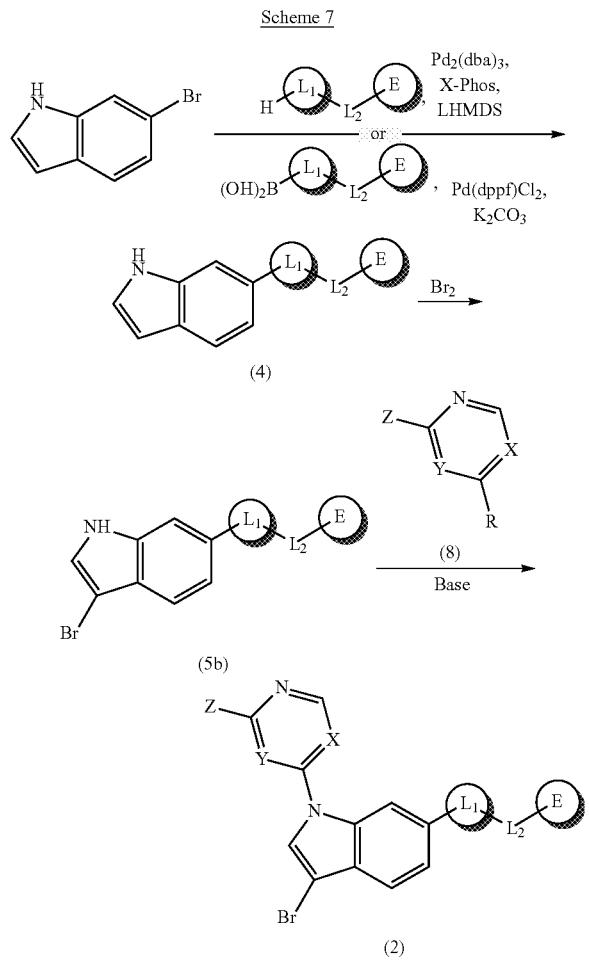

In Scheme 7, X, Y, Z, $L_1$, $L_2$ and E are the same as defined above, R is halogen or a leaving group, and the base is sodium tert-butoxide, sodium hydride, or the like.

The 1,3,6-substituted indole compound represented by Chemical Formula 1, a pharmaceutically acceptable salt thereof, a solvate thereof and a hydrate thereof may be used as an agent for preventing or treating diseases caused by abnormal cell growth because they exhibit superior inhibitory activity for various protein kinases, e.g., Raf, KDR, Fms, Tie2, SAPK2a, Ret, Abl, Abl(T315I), ALK, Aurora A, Bmx, CDK/cyclinE, Kit, Src, EGFR, EphA1, FGFR3, Flt3, Fms, IGF-1R, IKKb, IR, Itk, JAK2, KDR, Met, mTOR, PDGFRa, Plk1, Ret, Syk, Tie2 and TrtB. Examples of the diseases caused by abnormal cell growth include various cancers such as stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, or the like.

Accordingly, the present invention provides a pharmaceutical composition comprising the indole compound represented by Chemical Formula 1, a pharmaceutically acceptable salt thereof, a solvate thereof or a hydrate thereof as an active ingredient, and an agent for preventing and treating various cancers caused by abnormal cell growth.

The pharmaceutical composition of the present invention comprises the indole compound represented by Chemical Formula 1, a pharmaceutically acceptable salt thereof, a solvate thereof or a hydrate thereof as an active ingredient and may further include a commonly used, nontoxic, pharmaceutically acceptable carrier, adjuvant, excipient, or the like to prepare formulations commonly used in the pharmaceutical field, for example, formulations for oral administration such as tablet, capsule, troche, liquid, suspension, etc. and formulations for parenteral administration.

The excipient that may be used in the pharmaceutical composition of the present invention includes a sweetener, a binder, a solubilizer, a wetting agent, an emulsifier, an isotonic agent, an adsorbent, a disintegrant, an antioxidant, a preservative, a lubricant, a filler, an aromatic, or the like. For example, lactose, dextrose, sucrose, mannitol, sorbitol, cellulose, glycine, silica, talc, stearic acid, stearin, magnesium stearate, magnesium aluminum silicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, or the like may be used.

The administration dose of the compound according to the present invention may vary depending on the patient's age, body weight, sex and physical conditions, administration type, severity of disease, etc. Based on an adult patient weighing 70 kg, the administration dose may be in general 0.01 to 1,000 mg/day. As per the decision by a physician or a pharmacist, the administration may be made once or several times a day with predetermined time intervals.

PREPARATION EXAMPLES

The preparation examples will now be described. The following examples are for illustrative purposes only and not intended to limit the scope of this disclosure.

Preparation Example 1

6-bromo-1H-indole

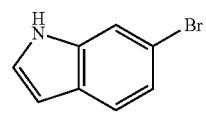

To a mixture solution of 4-bromo-2-nitrotoluene (2.00 g, 9.26 mmol) and dimethylformamide-dimethylacetal (3.68 mL, 27.8 mmol) in DMF (20 mL), pyrrolidine (1.16 mL, 13.9 mmol) was added at room temperature. After stirring at 110° C. for an hour, the mixture was cooled to room temperature and then water was added. After extracting 3 times with ether, the collected organic layer was dried with anhydrous magnesium sulfate and the concentrated. The resulting residue was subjected to the next reaction without purification. After adding 80% acetic acid aqueous solution (60 mL), the mixture was heated to 85° C. While adding zinc powder (5.27 g, 80.6 mmol) in small amounts, the mixture was stirred at 85° C. for 2 hours. After cooling to room temperature and filtering, followed by addition of water, the filtrate was extracted with ethyl acetate. The collected organic layer was washed with brine and concentrated by drying with anhydrous magnesium sulfate. The residue was purified by chromatography (silica gel, EA:Hx=1:20). The target compound (710 mg) was obtained as violet solid.

$^1$H NMR (400 MHz, DMSO-d$_6$) δ 11.21 (br, 1H), 7.56 (s, 1H), 7.49 (d, 1H), 7.36 (m, 1H), 7.10 (d, 1H), 6.44 (m, 1H).

Preparation Example 2 tert-butyl 4-(1H-indol-6-yl)piperazine-1-carboxylate

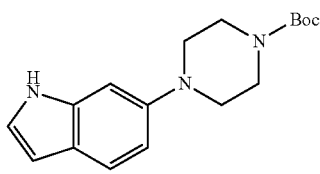 [SMILES: CC(C)(C)OC(=O)N1CCN(c2ccc3cc[nH]c3c2)CC1]

Pd$_2$(dba)$_3$ (30 mg, 0.026 mmol), tert-butyl piperazine-1-carboxylate (570 mg, 3.06 mmol), X-Phos (CAS Number: 564483-18-7, 40 mg, 0.077 mmol) and 6-bromo-1H-indole (500 mg, 2.55 mmol) were added to THF (2 mL) in a sealed reactor. After adding lithium hexamethyldisilazide (LHMDS; 1 M in THF, 5.61 mL, 5.6 mmol) at room temperature, the mixture solution was stirred at 65° C. for 24 hours in a sealed state. After cooling to room temperature, the reaction was terminated with saturated ammonium chloride aqueous solution. After extraction with ethyl acetate, the collected organic layer was washed with saturated sodium bicarbonate aqueous solution and brine and then concentrated by drying with anhydrous sodium sulfate. The residue was purified by chromatography (silica gel, EA:Hx=1:2). The target compound (334 mg) was obtained as white solid.

$^1$H NMR (400 MHz, DMSO-d$_6$) δ 10.79 (s, 1 H), 7.38 (d, J=8.8 Hz, 1 H), 7.15 (br s, 1 H), 6.85 (s, 1 H), 6.78 (d, J=8.8 Hz, 1 H), 6.28 (s, 1 H), 3.48 (t, J=4 Hz, 4 H), 3.01 (t, J=4 Hz, 4 H), 1.43 (s, 9 H).

Preparation Example 3

6-(4-methoxyphenyl)-1H-indole

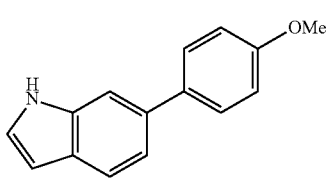 [SMILES: COc1ccc(-c2ccc3cc[nH]c3c2)cc1]

6-Bromo-1H-indole (1.00 g, 5.10 mmol) and potassium carbonate (1.41 g, 10.2 mmol) were dissolved in a mixture solution of DMF/water (4:1, 10.0 mL), and the gas included in the mixture solution was removed using ultrasonic waves and nitrogen gas. After sequentially adding 4-methoxyphenylboronic acid (853 mg, 5.61 mmol) and Pd(dppf)Cl$_2$ (416 mg, 0.51 mmol), the mixture was stirred at room temperature in a sealed state. 2 hours later, ethyl acetate and water were added and the reaction solution was filtered using a diatomite pad. After separation of the organic layer, the aqueous layer was extracted with ethyl acetate. The collected organic layer was concentrated by drying with anhydrous magnesium sulfate. The residue was purified by chromatography (silica gel, EA:Hx=1:4). The target compound was obtained as white solid.

$^1$H NMR (400 MHz, CDCl$_3$) δ 8.19 (br, 1H), 7.68 (d, 1H), 7.59 (d, 2H), 7.56 (s, 1H), 7.35 (m, 1H), 7.25 (m, 1H), 7.00 (d, 2H), 6.57 (m, 1H), 3.87 (s, 3H); MS m/z [M+1] 224.20.

Preparation Example 4

4-(1H-indol-6-yl)phenol

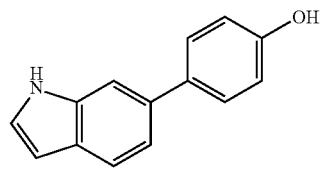 [SMILES: Oc1ccc(-c2ccc3cc[nH]c3c2)cc1]

The target compound was prepared as in Preparation Example 3 using suitable starting materials.

$^1$H NMR (400 MHz, DMSO-d$_6$) δ 11.07 (s, 1 H), 9.41 (s, 1 H), 7.56 (d, J=10.4 Hz, 1 H), 7.53 (s, 1 H), 7.48 (d, J=12 Hz, 1 H), 7.47 (d, J=11.6 Hz, 2 H), 7.20 (d, J=6.8 Hz, 1 H), 6.84 (d, J=11.6 hz, 2 H), 6.40 (s, 1 H).

Preparation Example 5

6-(3-nitrophenyl)-1H-indole

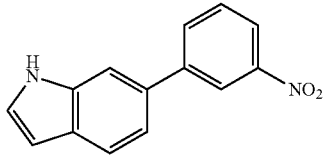 [SMILES: O=[N+]([O-])c1cccc(-c2ccc3cc[nH]c3c2)c1]

The target compound was prepared as in Preparation Example 3 using suitable starting materials.

$^1$H NMR (400 MHz, CDCl$_3$) δ 8.52 (m, 1H), 8.32 (br, 1H), 8.17 (dd, 1H), 7.98 (d, 1H), 7.76 (d, 1H), 7.71 (s, 1H), 7.60 (t, 1H), 7.41 (dd, 1H), 7.31 (m, 1H), 6.63 (m, 1H); MS m/z [M+1] 239.18.

Preparation Example 6

4-(3-bromo-1H-indol-6-yl)phenol

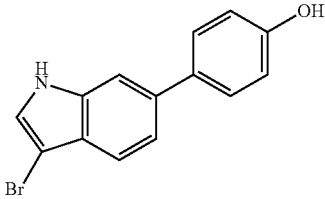 [SMILES: Oc1ccc(-c2ccc3c(Br)c[nH]c3c2)cc1]

A mixture solution of bromine (25 μL, 0.48 mmol) in DMF (1 mL) was added to a mixture solution of 4-(1H-indol-6-yl)phenol (100 mg, 0.48 mmol) in DMF (1 mL) at room temperature. After stirring for 1.5 hours at room temperature, followed by addition of icy water and addition of sodium thiosulfate, the mixture was stirred for 1 hour. Thus produced solid was filtered, washed with water and dried at room temperature. The target compound (136 mg) was obtained as white solid.

$^1$H NMR (400 MHz, DMSO-d$_6$) δ 11.45 (s, 1H), 9.47 (s, 1H), 7.53 (m, 1H), 7.52 (s, 1H), 7.47 (d, 2H), 7.41 (d, 1H), 7.33 (d, 1H), 6.84 (d, 2H); MS m/z [M+1] 287.17, 289.10.

Preparation Example 7

3-bromo-6-(3-nitrophenyl)-1H-indole

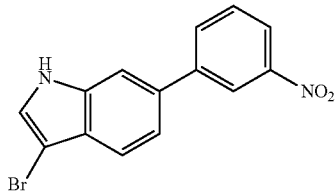 [SMILES: O=[N+]([O-])c1cccc(-c2ccc3c(Br)c[nH]c3c2)c1]

The target compound was prepared as in Preparation Example 6 using suitable starting materials.

$^1$H NMR (400 MHz, CDCl$_3$) δ 8.51 (s, 1H), 8.38 (hr 1H), 8.19 (d, 1H), 7.96 (d, 1H), 7.69 (d, 1H), 7.64 (s, 1H), 7.60 (d, 1H), 7.48 (d, 1H), 7.32 (d, 1H); MS m/z [M+1] 316.15, 318.10.

Preparation Example 8

3-bromo-6-(4-methoxyphenyl)-1H-indole

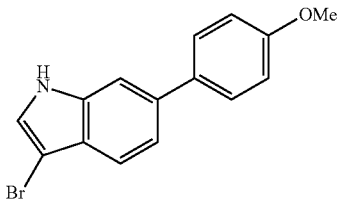 [SMILES: COc1ccc(-c2ccc3c(Br)c[nH]c3c2)cc1]

The target compound was prepared as in Preparation Example 6 using 6-(4-methoxyphenyl)-1H-indole (500 mg, 2.24 mmol) and bromine (115 μL, 2.24 mmol).

$^1$H NMR (400 MHz, CDCl$_3$) δ 8.21 (br, 1H), 7.61 (d, 1H), 7.57 (d, 2H), 7.53 (s, 1H), 7.43 (d, 1H), 7.24 (d, 1H), 7.00 (d, 2H), 3.87 (s, 3H); MS m/z [M+1] 301.01, 303.08.

EXAMPLES

The following examples exemplify the preparation of the compound represented by Chemical Formula 1 or a pharmaceutically acceptable thereof. However, the present invention is not limited thereto.

Example 1 tert-butyl 4-(1-(pyridin-4-yl)-1H-indol-6-yl)piperazine-1-carboxylate

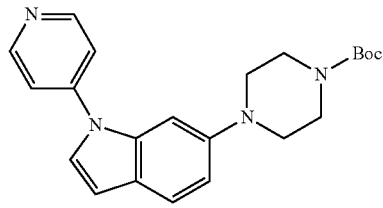 [SMILES: CC(C)(C)OC(=O)N1CCN(c2ccc3ccn(-c4ccncc4)c3c2)CC1]

tert-Butyl 4-(1H-indol-6-yl)piperazine-1-carboxylate (500 mg, 1.66 mmol), sodium tert-butoxide (447 mg, 4.65 mmol), 4-bromopyridine hydrochloride (355 mg, 1.83 mmol) and toluene (11 mL) were sequentially acted to a reactor. Then, the gas dissolved in the mixture was removed using ultrasonic waves and nitrogen gas. After adding 10% (w/w) palladium-carbon (Pd—C, 177 mg, 0.083 mmol) and 2,2'-bis(diphenylphosphino)-1,1'-binaphthyl (BINAP; 52 mg, 0.083 mmol), the mixture was stirred at 100° C. for 24 hours in a sealed state. After cooling to room temperature and filtering using a diatomite pad, water was added and the mixture was extracted with ethyl acetate. The collected organic layer was washed with brine and concentrated under reduced pressure by drying with anhydrous sodium sulfate. The residue was purified by chromatography (silica gel, EA:Hx=1:1→EA only). The target compound (369 mg, 59%) was obtained as white solid.

$^1$H NMR (400 MHz, DMSO-d$_6$) δ 8.68 (d, J=6 Hz, 2 H), 7.69 (d, J=6 Hz, 2 H), 7.64 (d, J=3.2 hz, 1 H), 7.52 (d, J=8.4 Hz, 1 H), 7.36 (d, J=4.8 Hz, 1 H), 7.33 (dd, J=2, 11.2 Hz, 1 H), 6.73 (d, J=4.8 Hz, 1 H).

Example 2 tert-butyl 4-(3-bromo-1-(pyridin-4-yl)-1H-indol-6-yl)piperazine-1-carboxylate

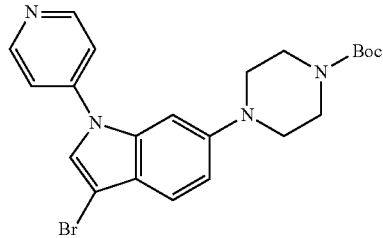 [SMILES: CC(C)(C)OC(=O)N1CCN(c2ccc3c(Br)cn(-c4ccncc4)c3c2)CC1]

N-Bromosuccinimide (64.4 mg, 0.36 mmol) was added to a mixture solution of tert-butyl 4-(1-(pyridin-4-yl)-1H-indol-6-yl)piperazine-1-carboxylate (137 mg, 0.36 mmol) in THF (12 mL) at −78° C. After stirring at −78° C. for 2 hours, the mixture was further stirred at 0° C. for 1 hour and then pyridine (88 μL, 1.09 mmol) was added. After filtering using a diatomite pad, the solution was adsorbed by adding silica gel. Purification by chromatography (silica gel, EA:Hx=4:1) yielded the target compound (49.1 mg, 30%) as white solid.

$^1$H NMR (400 MHz, DMSO-d$_6$) δ 8.82 (d, J=6 Hz, 2 H), 7.57 (d, J=6 Hz, 2 H), 7.46 (d, J=8.8 Hz, 1 H), 6.95 (dd, J=2, 8.8 Hz, 1 H), 6.83 (s, 1 H), 6.66 (s, 1 H), 3.39 (br s, 4 H), 3.01 (br s, 4 H), 1.39 (s, 9 H).

Example 3

4-(1-(pyridin-4-yl)-1H-indol-6-yl)phenol

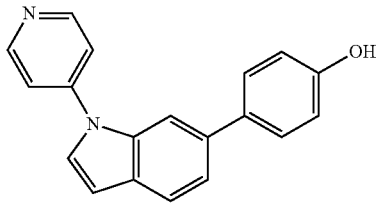 [SMILES: Oc1ccc(-c2ccc3ccn(-c4ccncc4)c3c2)cc1]

The target compound was prepared as in Example 1 using 4-(1H-indol-6-yl)phenol (200 mg, 0.96 mmol) and 4-bromopyridine hydrochloride (205 mg, 1.06 mmol).

$^1$H NMR (400 MHz, DMSO-d$_6$) δ 9.49 (s, 1 H), 8.71 (d, J=4.8 Hz, 2 H), 7.87 (s, 1 H), 7.82 (d, J=3.6 Hz, 2 H), 7.77 (d, J=4.8 Hz, 2 H), 7.70 (d, J=8 Hz, 1 H), 7.54 (d, J=8.4 Hz, 2H), 7.41 (br d, J=8 Hz, 1 H), 6.85 (d, J=8 Hz, 2 H), 6.80 (d, J=3.2 Hz, 1 H).

Example 4

4-(3-bromo-1-(pyridin-4-yl)-1H-indol-6-yl)phenol

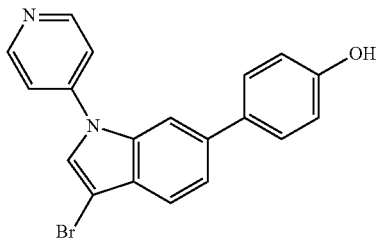 [SMILES: Oc1ccc(-c2ccc3c(Br)cn(-c4ccncc4)c3c2)cc1]

N-Bromosuccinimide (8.1 mg, 0.046 mmol) was added to a mixture solution of tert-butyl 4-(1-(pyridin-4-yl)-1H-indol-6-yl)phenol (10 mg, 0.035 mmol) in THF (0.5 mL) mixture solution at −78° C. After stirring at −78° C. for 2 hours, the mixture was further stirred at 0° C. for 1 hour and then pyridine (8.5 μL, 0.105 mmol) was added. After stirring at room temperature for 30 minutes, water was added and the mixture was extracted with ethyl acetate. The collected organic layer was washed with saturated sodium bicarbonate solution and brine, and then concentrated under reduced pressure by drying with anhydrous magnesium sulfate. The target compound was obtained as white solid.

MS m/z [M+1] 365.11, 367.13.

Example 5

1-(2-(methylthio)pyrimidin-4-yl)-6-(3-nitrophenyl)-1H-indole

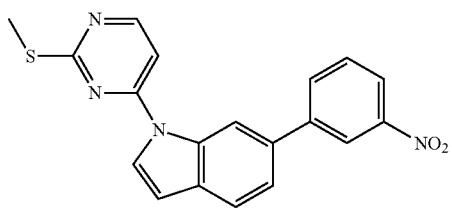 [SMILES: CSc1nccc(-n2ccc3ccc(-c4cccc([N+](=O)[O-])c4)cc32)n1]

Sodium hydride (60% in mineral oil, 40 mg, 0.98 mmol) was added to a mixture solution of 6-(3-nitrophenyl)-1H-indole (117 mg, 0.49 mmol) in DMF (2 mL) at room temperature. 10 minutes later, 4-chloro-2-(methylthio)pyrimidine (68 μL, 0.59 mmol) was added. After stirring at room temperature for 30 minutes, water was added. Thus produced solid was filtered and dried. The target compound (102 mg) was obtained as white solid.

$^1$H NMR (400 MHz, CDCl$_3$) δ 8.95 (m, 1H), 8.56 (m, 1H), 8.53 (d, 1H), 8.21 (d, 1H), 8.01 (d, 1H), 7.76 (s, 1H), 7.74 (d, 1H), 7.65 (t, 1H), 7.54 (dd, 1H), 7.07 (d, 1H), 6.83 (d, 1H), 2.73 (s, 3H); MS m/z [M+1] 363.22.

Example 6

6-(3-nitrophenyl)-1-(pyridin-4-yl)-1H-indole

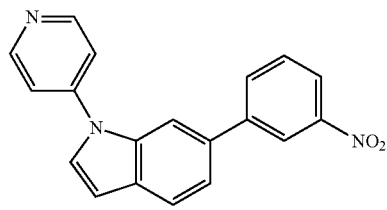 [SMILES: O=[N+]([O-])c1cccc(-c2ccc3ccn(-c4ccncc4)c3c2)c1]

The target compound was prepared as in Example 1 using 6-(3-nitrophenyl)-1H-indole (98 mg, 0.412 mmol) and 4-bromopyridine hydrochloride (88 mg, 0.453 mmol).

$^1$H NMR (400 MHz, DMSO-d$_6$) δ 8.73 (d, 2H), 8.50 (s, 1H), 8.23 (d, 1H), 8.08 (s, 1H), 7.92 (d, 1H), 7.84 (s, 1H), 7.83 (d, 2H), 7.74 (t, 1H), 7.59 (d, 1H), 6.88 (d, 1H).

Example 7

3-bromo-6-(3-nitrophenyl)-1-(pyridin-4-yl)-1H-indole

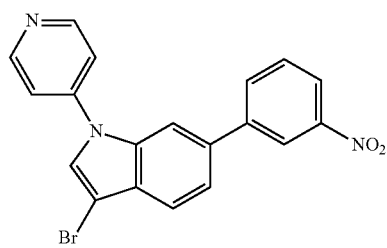 [SMILES: O=[N+]([O-])c1cccc(-c2ccc3c(Br)cn(-c4ccncc4)c3c2)c1]

The target compound was prepared as in Example 1 using 6-(3-nitrophenyl)-1-(pyridin-4-yl)-1H-indole (70 mg, 0.222 mmol) and 4-bromopyridine hydrochloride (40 mg, 0.222 mmol).

$^1$H NMR (400 MHz, DMSO-d$_6$) δ 8.75 (d, 2H), 8.52 (s, 1H), 8.26-8.21 (m, 3H), 8.10 (s, 1H), 7.85 (d, 2H), 7.75 (t, 1H), 7.72-7.70 (m, 2H).

Example 8

3-bromo-1-(2-(methylthio)pyrimidin-4-yl)-6-(3-nitrophenyl)-1H-indole

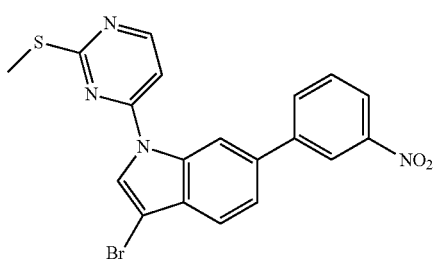 [SMILES: CSc1nccc(-n2cc(Br)c3ccc(-c4cccc([N+](=O)[O-])c4)cc32)n1]

Sodium hydride (60% in mineral oil, 38 mg, 0.946 mmol) was added to a mixture solution of 3-bromo-6-(3-nitrophenyl)-1H-indole (100 mg, 0.315 mmol) in anhydrous DMF (2 mL) at room temperature. 10 minutes later, 4-chloro-2-(methylthio)pyrimidine (44 µL, 0.378 mmol) was added. After stirring at room temperature for 2 hours, water was added. Thus produced solid was filtered and dried. The target compound (140 mg) was obtained as white solid.

MS m/z [M+1] 441.11, 443.13.

Example 9

3-bromo-1-(6-chloropyrimidin-4-yl)-6-(3-nitrophenyl)-1H-indole

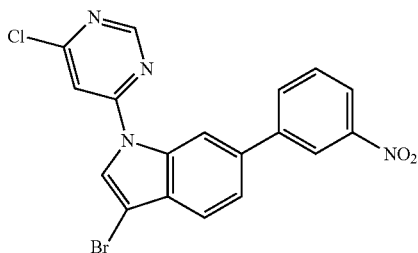 [SMILES: O=[N+]([O-])c1cccc(-c2ccc3c(Br)cn(-c4cc(Cl)ncn4)c3c2)c1]

Sodium hydride (60% in mineral oil, 114 mg, 2.84 mmol) was added to a mixture solution of 3-bromo-6-(3-nitrophenyl)-1H-indole (450 mg, 1.42 mmol) and 4,6-dichloropyrimidine (212 mg, 1.42 mmol) in anhydrous DMF (10 mL) at room temperature. After stirring at room temperature for 5 hours, followed by addition of ice, the mixture was added to icy water. After stirring at room temperature for 12 hours, the produced solid was filtered, washed with water, and then dried. The target compound (600 mg) was obtained as yellow solid.

$^1$H NMR (400 MHz, CDCl$_3$) δ8.96 (s, 1H), 8.93 (s, 1H), 8.54 (s, 1H), 8.25 (dd, 1H), 8.01 (d, 1H), 7.79 (s, 1H), 7.72 (d, 1H), 7.68 (t, 1H), 7.63 (d, 1H), 7.41 (s, 1H); MS m/z [M+1] 429.05, 431.03, 433.01.

Example 10

6-(3-bromo-6-(3-nitrophenyl)-1H-indol-1-yl)-N-methylpyrimidin-4-amine

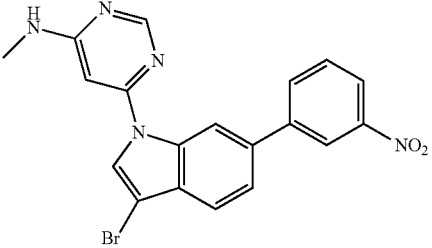 [SMILES: CNc1cc(-n2cc(Br)c3ccc(-c4cccc([N+](=O)[O-])c4)cc32)ncn1]

DMF (10 mL) was added to a mixture of 3-bromo-1-(6-chloropyrimidin-4-yl)-6-(3-nitrophenyl)-1H-indole (500 mg, 1.16 mmol), methylamine hydrochloride (393 mg, 5.82 mmol) and potassium carbonate (1.60 g, 11.6 mmol). After stirring at 80° C. for 3 hours and then cooling to room temperature, the reaction solution was added to icy water. After stirring at room temperature for 15 hours, thus produced solid was filtered, washed with water and then dried. The target compound (500 mg) was obtained as yellow solid.

$^1$H NMR (400 MHz, CDCl$_3$) δ 8.74 (s, 1H), 8.57 (s, 1H), 8.54 (m, 1H), 8.22 (d, 1H), 8.01 (d, 1H), 7.81 (s, 1H), 7.70 (d, 1H), 7.65 (t, 1H), 7.57 (d, 1H) 6.33 (s, 1H), 3.07 (d, 3H); MS m/z [M+1] 424.16, 426.16.

Example 11

3-bromo-1-(6-chloropyrimidin-4-yl)-6-(4-methoxyphenyl)-1H-indole

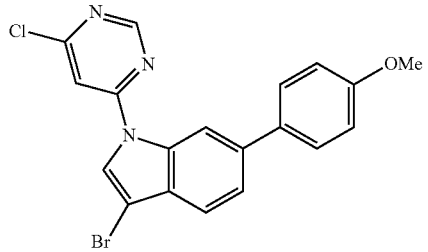 [SMILES: COc1ccc(-c2ccc3c(Br)cn(-c4cc(Cl)ncn4)c3c2)cc1]

The target compound was prepared as in Example 9 using 3-bromo-6-(4-methoxyphenyl)-1H-indole (500 mg, 1.65 mmol) and 4,6-dichloropyrimidine (247 mg, 1.65 mmol).

$^1$H NMR (400 MHz, CDCl$_3$) δ8.91 (s, 1H), 8.74 (s, 1H), 7.76 (s, 1H), 7.64 (d, 1H), 7.62 (d, 2H), 7.57 (d, 1H), 7.40 (s, 1H), 7.04 (d, 2H), 3.89 (s, 3H); MS m/z [M+1] 413.89, 415.88.

Example 12

6-(3-bromo-6-(4-methoxyphenyl)-1H-indol-1-yl)-N-methylpyrimidin-4-amine

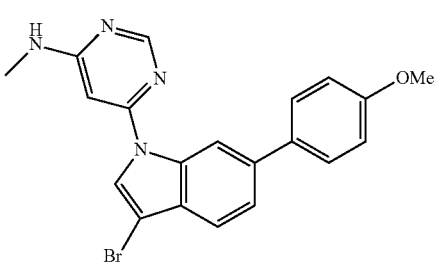 [SMILES: CNc1cc(-n2cc(Br)c3ccc(-c4ccc(OC)cc4)cc32)ncn1]

The target compound was prepared as in Example 10 using 3-bromo-1-(6-chloropyrimidin-4-yl)-6-(4-methoxyphenyl)-1H-indole (400 mg, 0.96 mmol) and methylamine hydrochloride (326 mg, 4.8 mmol).

$^1$H NMR (400 MHz, CDCl$_3$) δ8.59 (s, 1H), 8.55 (s, 1H), 7.79 (s, 1H), 7.62 (d, 1H), 7.60 (d, 2H), 7.51 (d, 1H), 7.02 (d, 2H), 6.35 (s, 1H), 5.13 (br, 1H), 3.86 (s, 3H), 3.04 (d, 3H); MS m/z [M+1] 408.96, 410.98.

Example 13 tert-butyl 4-(3-(4-methoxyphenyl)-1-(pyridin-4-yl)-1H-indol-6-yl)piperazine-1-carboxylate

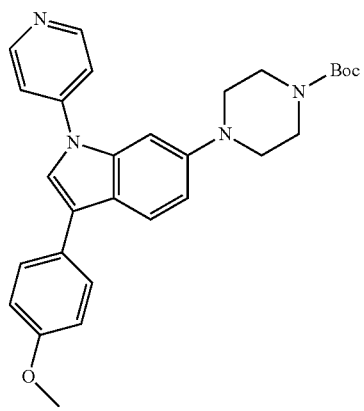 [SMILES: COc1ccc(-c2cn(-c3ccncc3)c3cc(N4CCN(C(=O)OC(C)(C)C)CC4)ccc23)cc1]

DMF/water (4:1, 2 mL) was added to a mixture of tert-butyl 4-(3-bromo-1-(pyridin-4-yl)-1H-indol-6-yl)piperazine-1-carboxylate (29 mg, 0.0636 mmol), potassium carbonate (18 mg, 0.13 mmol) and 4-methoxyphenylboronic acid (11 mg, 0.070 mmol) and the dissolved gas was removed. After adding Pd(dppf) Cl$_2$ (10.4 mg, 0.013 mmol), the mixture was stirred at room temperature for 14 hours. After adding ethyl acetate and water, the mixture was filtered using a diatomite pad. After separation of the organic layer, the aqueous layer was extracted with ethyl acetate. The collected organic layer was washed with brine and concentrated under reduced pressure by drying with anhydrous magnesium sulfate. The residue was purified by chromatography (silica gel, EA:Hx=1:4 1:1). The target compound (31 mg) was obtained as white solid.

$^1$H NMR (400 MHz, DMSO-d$_6$) δ 8.65 (d, J=6 Hz, 2 H), 7.51 (d, J=8.4 Hz, 1 H), 7.28 (d, 6 Hz, 2 H), 7.13 (d, J=8.8 Hz, 2 H), 6.96 (dd, J=1.6, 10.4 Hz, 1 H), 6.88 (d, J=8.8 Hz, 2 H), 6.82 (s, 1 H), 6.71 (s, 1 H), 3.74 (s, 3 H), 3.46 (br s, 4 H), 3.02 (br s, 4 H), 1.40 (s, 9 H).

Example 14

3-(4-methoxyphenyl)-6-(piperazin-1-yl)-1-(pyridin-4-yl)-1H-indole

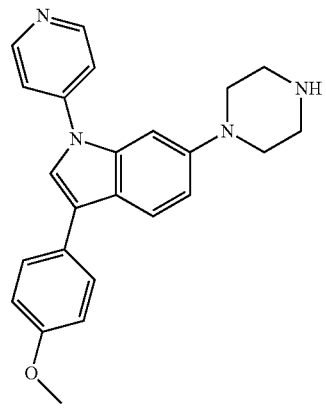 [SMILES: COc1ccc(-c2cn(-c3ccncc3)c3cc(N4CCNCC4)ccc23)cc1]

Trifluoroacetic acid (46 μL, 0.059 mmol) was added to a mixture solution of tert-butyl 4-(3-(4-methoxyphenyl)-1-(pyridin-4-yl)-1H-indol-6-yl)piperazine-1-carboxylate (29 mg, 0.059 mmol) in methylene chloride (1 mL) at room temperature. After stirring for 3 hours, the reaction solution was concentrated under reduced pressure. After adding ethyl acetate and saturated sodium bicarbonate aqueous solution, the mixture was extracted with ethyl acetate. The collected organic layer was washed with brine and concentrated under reduced pressure by drying with anhydrous magnesium sulfate. The target compound (14 mg, 64%) was obtained as yellow solid.

$^1$H NMR (400 MHz, DMSO-d$_6$) δ 8.65 (br d, J=6 Hz, 2 H), 7.48 (d, J=8.8 Hz, 1 H), 7.28 (br d, J=6 Hz, 2 H), 7.13 (d, =8.8 Hz, 2 H), 6.92 (dd, J=2, 8.8 Hz, 1 H), 6.88 (d, J=8.8 Hz, 2 H), 6.77 (s, 1 H), 6.69 (s, 1 H), 3.73 (s, 3 H), 2.97 (br s, 4 H), 2.81 (br s, 4 H).

Example 15

4-(6-(piperazin-1-yl)-1-(pyridin-4-yl)-1H-indol-3-yl)phenol

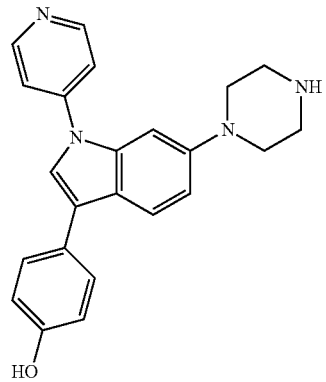 [SMILES: Oc1ccc(-c2cn(-c3ccncc3)c3cc(N4CCNCC4)ccc23)cc1]

Boron tribromide (BBr₃, 17 μL, 0.182 mmol) was added to a mixture solution of 3-(4-methoxyphenyl)-6-(piperazin-1-yl)-1-(pyridin-4-yl)-1H-indole (14 mg, 0.036 mmol) in methylene chloride (0.5 mL) at −78° C. After stirring at room temperature for 15 hours, the reaction solution was added to a mixture solution of saturated sodium bicarbonate aqueous solution and ethyl acetate and then extracted with ethyl acetate. The collected organic layer was washed with brine and concentrated under reduced pressure by drying with anhydrous magnesium sulfate. The target compound (12 mg) was obtained as yellow solid.

¹H NMR (400 MHz, DMSO-d₆) δ 9.60 (br s, 1 H), 8.64 (d, J=6.4 Hz, 2 H), 7.46 (d, J=11.2 Hz, 1 H), 7.26 (d, J=6.4 Hz, 2 H), 7.01 (d, J=11.6 Hz, 2 H), 6.91 (d, J=11.2 Hz, 1 H), 6.77 (s, 1 H), 6.68 (d, J=11.2 Hz, 2 H), 6.63 (s, 1 H), 2.97 (br s, 4 H), 2.80 (br s, 4 H).

Example 16 tert-butyl 4-(3-(4-(tert-butoxycarbonyloxy)phenyl)-1-(pyridin-4-yl)-1H-indol-6-yl)piperazine-1-carboxylate

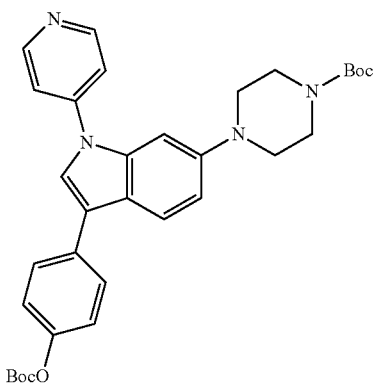

4-(6-(piperazin-1-yl)-1-(pyridin-4-yl)-1H-indol-3-yl)phenol (13 mg, 0.035 mmol) and methylene chloride (2 mL) were added to a reactor and a catalytic amount of N,N-dimethylaminopyridine, triethylamine (6 μL, 0.039 mmol) and (Boc)₂O were sequentially added at 0° C. After stirring at 0° C. for 1 hour and then at room temperature for 3 hours, water and ethyl acetate were added. After extraction with ethyl acetate, the collected organic layer was washed with brine and concentrated under reduced pressure by drying with anhydrous magnesium sulfate. The residue was purified by chromatography (silica gel, EA only). The target compound (12 mg, 60%) was obtained as yellow solid.

¹H NMR (400 MHz, DMSO-d₆) δ 8.66 (br d, J=6.4 Hz, 2 H), 7.54 (d, J=8.8 Hz, 1 H), 7.31 (br d, J=6.4 Hz, 2 H), 7.24 (d, J=8.8 Hz, 2 H), 7.15 (d, J=8.8 Hz, 2 H), 6.98 (br d, J=10.4 Hz, 1 H), 6.83 (br s, 2 H), 3.45 (br s, 4 H), 3.04 (br s, 4 H), 1.48 (s, 9 H), 1.41 (s, 9 H).

Example 17 tert-butyl 4-(3-(4-hydroxyphenyl)-1-(pyridin-4-yl)-1H-indol-6-yl)piperazine-1-carboxylate

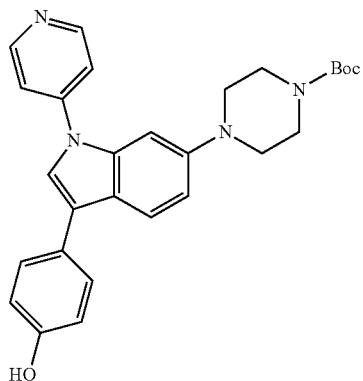 [SMILES: CC(C)(C)OC(=O)N1CCN(c2ccc3c(-c4ccc(O)cc4)cn(-c4ccncc4)c3c2)CC1]

2 N sodium hydroxide aqueous solution (18 μL, 0.035 mmol) was added to a mixture solution of tert-butyl 4-(3-(4-(tert-butoxycarbonyloxy)phenyl)-1-(pyridin-4-yl)-1H-indol-6-yl)piperazine-1-carboxylate (10 mg, 0.018 mmol) in methanol (0.5 mL) at room temperature. After stirring at room temperature for 3.5 hours, followed by addition of water, the mixture was extracted with ethyl acetate. The collected organic layer was washed with brine and concentrated under reduced pressure by drying with anhydrous magnesium sulfate. The target compound was obtained as white solid.

¹H NMR (400 MHz, DMSO-d₆) δ 8.64 (br d, J=6 Hz, 2 H), 7.49 (d, J=8.8 Hz, 1 H), 7.26 (br d, J=6 Hz, 2 H), 7.01 (d, J=8.8 Hz, 2 H), 6.93 (d, J=8.4 Hz, 1 H), 6.82 (s, 1 H), 6.69 (d, J=8.8 Hz, 2 H), 6.65 (s, 1 H), 3.43 (br s, 4 H), 3.01 (br s, 4 H), 1.40 (s, 9 H).

Example 18 tert-butyl 4-(3-(4-(2-(dimethylamino)ethoxy)phenyl)-1-(pyridin-4-yl)-1H-indol-6-yl)piperazine-1-carboxylate

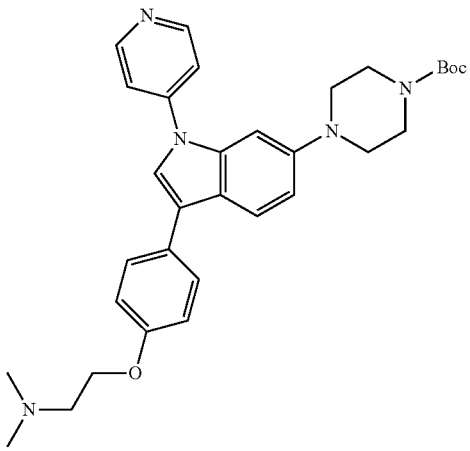 [SMILES: CN(C)CCOc1ccc(-c2cn(-c3ccncc3)c3cc(N4CCN(C(=O)OC(C)(C)C)CC4)ccc23)cc1]

2-Chloro-N,N-dimethylethylamine hydrochloride (7.3 mg, 0.051 mmol) and cesium carbonate (33 mg, 0.101 mmol) were added to a mixture solution of tert-butyl 4-(3-(4-hydroxyphenyl)-1-(pyridin-4-yl)-1H-indol-6-yl)piperazine-1-carboxylate (12 mg, 0.025 mmol) in DMF (1 mL). After room temperature stirring at room temperature for 16 hours, followed by addition of water, the mixture was extracted with ethyl acetate. The collected organic layer was washed with brine and concentrated under reduced pressure by drying with anhydrous magnesium sulfate. The target compound was obtained as white solid.

$^1$H NMR (400 MHz, DMSO-$d_6$) δ 8.65 (d, J=6.4 Hz, 2 H), 7.51 (d, J=11.2 Hz, 1 H), 7.28 (d, J=8 Hz, 2 H), 6.96 (br d, J=13.2 Hz, 1 H), 6.88 (d, J=11.2 Hz, 2 H), 6.83 (br s, 1 H), 6.71 (s, 1 H), 4.02 (t, J=7.2 Hz, 2 H), 3.45 (br s, 4 H), 3.02 (br s, 4 H), 2.59 (t, J=7.2 Hz, 2 H), 2.19 (s, 6 H), 1.41 (s, 9 H).

Example 19

N,N-dimethyl-2-(4-(6-(piperazin-1-yl)-1-(pyridin-4-yl)-1H-indol-3-yl)phenoxy)ethanamine

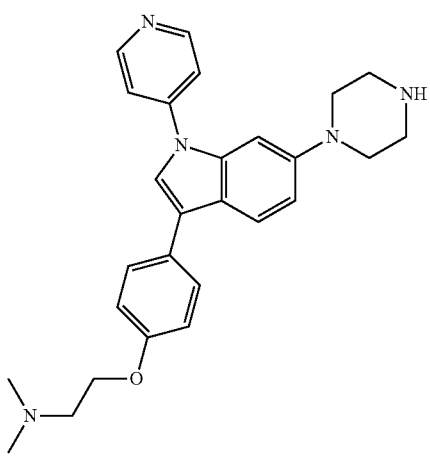 [SMILES: CN(C)CCOc1ccc(-c2cn(-c3ccncc3)c3cc(N4CCNCC4)ccc23)cc1]

Trifluoroacetic acid (0.2 mL) was added to a mixture solution of tert-butyl 4-(3-(4-(2-(dimethylamino)ethoxy)phenyl)-1-(pyridin-4-yl)-1H-indol-6-yl)piperazine-1-carboxylate (4.1 mg, 7.6 μmol) in methylene chloride (0.2 mL) at room temperature. After stirring for 15 hours, the reaction solution was concentrated under reduced pressure. After adding ethyl acetate and saturated sodium bicarbonate aqueous solution, the mixture was extracted with ethyl acetate. The collected organic layer was washed with brine and concentrated under reduced pressure by drying with anhydrous magnesium sulfate. The target compound was obtained as white solid.

$^1$H NMR (400 MHz, DMSO-$d_6$) δ 8.65 (br d, J=6 Hz, 2 H), 7.54 (d, J=8.8 Hz, 1 H), 7.30 (br d, J=6 Hz, 2 H), 7.13 (d, J=8.8 Hz, 2 H), 6.97 (dd, J=3, 8.4 Hz, 1 H), 6.89 (d, J=8.8 Hz, 2 H), 6.83 (s, 1 H), 6.73 (s, 1 H), 4.05 (t, J=6.8 Hz, 2 H), 3.22 (br s, 4 H), 3.19 (br s, 4 H), 2.51 (t, J=6.8 Hz, 2 H), 2.27 (s, 6 H).

Example 20

3-(4-methoxyphenyl)-6-(3-nitrophenyl)-1-(pyridin-4-yl)-1H-indole

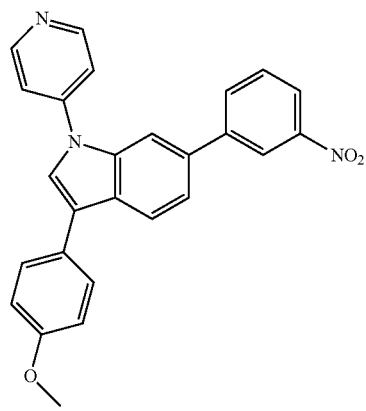 [SMILES: COc1ccc(-c2cn(-c3ccncc3)c3cc(-c4cccc([N+](=O)[O-])c4)ccc23)cc1]

The target compound was prepared as in Example 13 using 3-bromo-6-(3-nitrophenyl)-1-(pyridin-4-yl)-1H-indole (97 mg, 0.222 mmol) and 4-methoxyphenylboronic acid (37 mg, 0.244 mmol).

$^1$H NMR (400 MHz, DMSO-$d_6$) δ 8.76 (d, 2H), 8.49 (s, 1H), 8.26 (d, 1H), 8.21 (d, 1H), 8.16 (s, 1H), 8.05 (d, 1H), 7.9 (d, 2H), 7.78*t, 1H), 7.73 (d, 2H), 7.67 (d, 1H), 7.10 (d, 1H), 3.78 (s, 3H).

Example 21

4-(6-(3-nitrophenyl)-1-(pyridin-4-yl)-1H-indol-3-yl)phenol

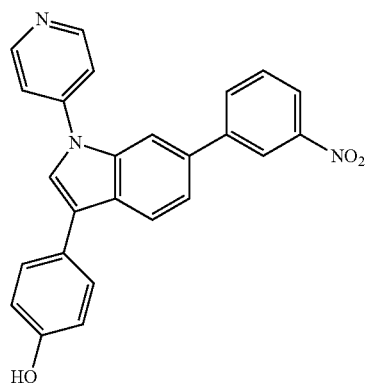 [SMILES: O=[N+]([O-])c1cccc(-c2ccc3c(-c4ccc(O)cc4)cn(-c4ccncc4)c3c2)c1]

The target compound was prepared as in Example 15 using 3-(4-methoxyphenyl)-6-(3-nitrophenyl)-1-(pyridin-4-yl)-1H-indole (58 mg, 0.138 mmol) and boron tribromide (BBr$_3$, 65 μL, 0.691 mmol).

$^1$H NMR (400 MHz, DMSO-$d_6$) δ 9.53 (s, 1H), 8.75 (d, 2H), 8.52 (m, 1H), 8.26 (d, 1H), 8.21 (d, 1H), 8.15 (s, 1H), 8.09 (s, 1H), 8.03 (d, 1H), 7.89 (d, 2H), 7.78 (t, 1H), 7.66 (d, 1H), 7.61 (d, 2H), 6.92 (d, 2H).

Example 22

4-(6-(3-aminophenyl)-1-(pyridin-4-yl)-1H-indol-3-yl)phenol

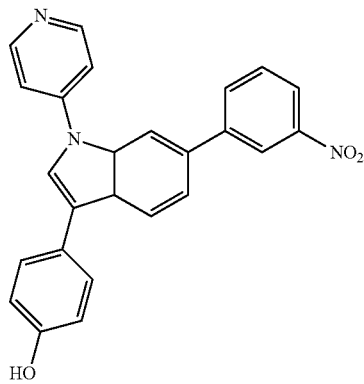 [SMILES: O=[N+]([O-])c1cccc(C2=CC3C(C=C2)C(c2ccc(O)cc2)=CN3c2ccncc2)c1]

Methanol (2 mL) was added to 4-(6-(3-nitrophenyl)-1-(pyridin-4-yl)-1H-indol-3-yl)phenol (4.6 mg, 0.0113 mmol) and 10% (w/w) palladium-carbon (Pd—C, 5.0 mg). The mixture was stirred at room temperature for 12 hours under hydrogen gas (1 atm). The reaction solution was filtered using a diatomite pad and concentrated under reduced pressure. The target compound was obtained as brown solid.

$^1$H NMR (400 MHz, DMSO-$d_6$) δ9.50 (s, 1H), 8.74 (d, 2H), 8.01 (s, 1H), 7.94 (d, 1H), 7.91 (s, 1H), 7.83 (d, 2H), 7.60 (d, 2H), 7.47 (d, 1H), 7.11 (t, 1H), 6.90 (d, 2H), 6.89 (s, 1H), 6.82 (d, 1H), 6.55 (d, 1H), 5.15 (s, 2H).

Example 23

N,N-dimethyl-2-(4-(6-(3-nitrophenyl)-1-(pyridin-4-yl)-1H-indol-3-yl)phenoxy)ethanamine

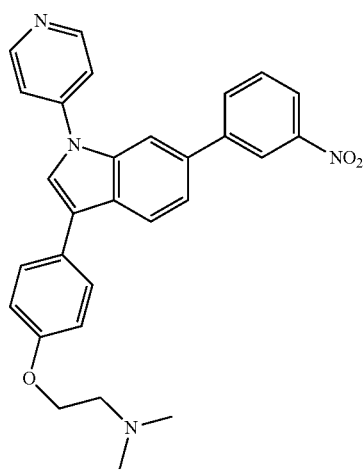

The target compound was prepared as in Example 18 using 4-(6-(3-nitrophenyl)-1-(pyridin-4-yl)-1H-indol-3-yl)phenol (32 mg, 0.079 mmol), 2-chloro-N,N-dimethylethylamine hydrochloride (34 mg, 0.237 mmol) and cesium carbonate (154 mg, 0.237 mmol).

$^1$H NMR (400 MHz, DMSO-$d_6$) δ8.76 (d, 2H), 8.53 (t, 1H), 8.26 (d, 1H), 8.21 (dd, 1H), 8.17 (s, 1H), 8.14 (s, 1H), 8.05 (d, 1H), 7.91 (d, 2H), 7.78 (t, 1H), 7.72 (d, 2H), 7.68 (dd, 1H), 7.10 (d, 2H), 4.13 (t, 2H), 2.67 (t, 2H), 2.26 (s, 6H).

Example 24

3-(3-(4-(2-(dimethylamino)ethoxy)phenyl)-1-(pyridin-4-yl)-1H-indol-6-yl)benzenamine

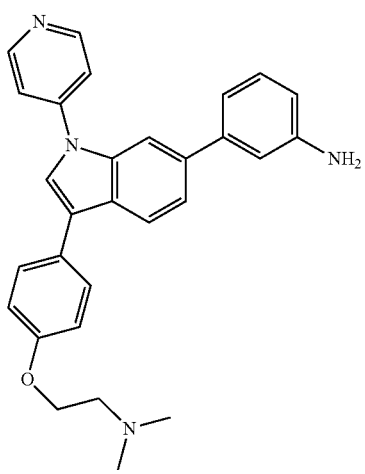 [SMILES: CN(C)CCOc1ccc(-c2cn(-c3ccncc3)c3cc(-c4cccc([N+](=O)[O-])c4)ccc23)cc1]

The target compound was prepared as in Example 22 using N,N-dimethyl-2-(4-(6-(3-nitrophenyl)-1-(pyridin-4-yl)-1H-indol-3-yl)phenoxy)ethanamine (7.5 mg, 0.016 mmol).

$^1$H NMR (400 MHz, DMSO-$d_6$) δ8.75 (d, 2H), 8.08 (s, 1H), 7.96 (d, 1H), 7.92 (s, 1H), 7.84 (d, 2H), 7.71 (d, 2H), 7.48 (d, 1H), 7.10 (t, 1H), 7.08 (d, 2H), 6.90 (s, 1H), 6.88 (d, 1H), 6.55 (d, 1H), 5.15 (s, 2H), 4.13 (t, 2H), 2.67 (t, 2H), 2.26 (s, 6H).

Example 25

N-(3-(3-(4-(2-(dimethylamino)ethoxy)phenyl)-1-(pyridin-4-yl)-1H-indol-6-yl)phenyl)acetamide

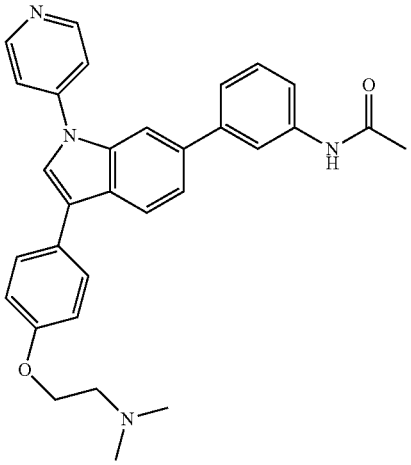 [SMILES: CC(=O)Nc1cccc(-c2ccc3c(-c4ccc(OCCN(C)C)cc4)cn(-c4ccncc4)c3c2)c1]

Acetic anhydride (4.8 μL, 0.5.1 μmol) was added to a mixture solution of 3-(3-(4-(2-(dimethylamino)ethoxy)phenyl)-1-(pyridin-4-yl)-1H-indol-6-yl)benzenamine (2.2 mg, 4.9 µmol) in pyridine (0.4 mL) at room temperature. After stirring for 15 hours at room temperature, the reaction solution was added to saturated sodium bicarbonate aqueous solution and then extracted with ethyl acetate. The collected organic layer was washed with brine and concentrated under reduced pressure by drying with anhydrous magnesium sulfate. The residue was purified by chromatography (preparative TLC, DCM:MeOH=10:1). The target compound (1.5 mg) was obtained as white solid.

$^1$H NMR (400 MHz, DMSO-$d_6$) δ10.03 (s, 1H), 8.75 (d, 2H), 8.11 (s, 1H), 8.01 (d, 1H), 7.97 (s, 1H), 8.85 (d, 2H), 7.72 (d, 2H), 7.53 (d, 1H), 7.50 (d, 1H), 7.40 (t, 1H), 7.39 (s, 1H), 7.09 (d, 2H), 6.55 (d, 1H), 4.13 (t, 2H), 2.67 (t, 2H), 2.26 (s, 6H), 2.06 (s, 3H).

Example 26

6-(6-(4-methoxyphenyl)-3-(3-nitrophenyl)-1H-indol-1-yl)-N-methylpyrimidin-4-amine

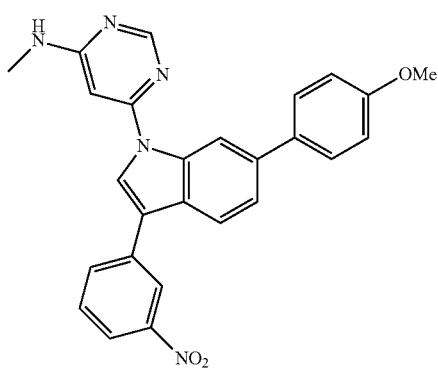 [SMILES: CNc1cc(-n2cc(-c3cccc([N+](=O)[O-])c3)c3ccc(-c4ccc(OC)cc4)cc32)ncn1]

DMF (5 mL) was added to a mixture of 6-(3-bromo-6-(4-methoxyphenyl)-1H-indol-1-yl)-N-methylpyrimidin-4-amine (200 mg, 0.49 mmol), $K_3PO_4$ (312 mg, 0.885 mmol) and 3-nitrophenylboronic acid (123 mg, 0.74 mmol) and then the dissolved gas was removed. After adding Pd(PPh$_3$)$_4$ (85 mg, 0.075 mmol), the mixture was stirred at 100° C. for 4 hours. After adding ethyl acetate and water and filtering using a diatomite pad, the organic layer was separated and the aqueous layer was extracted with ethyl acetate. The collected organic layer was washed with brine and concentrated under reduced pressure by drying with anhydrous magnesium sulfate. The residue was purified by chromatography (silica gel, EA:Hx=1:4-1:1). The target compound (70 mg) was obtained as white solid.

$^1$H NMR (400 MHz, CDCl$_3$) δ 8.60 (s, 1H), 8.59 (s, 1H), 8.58 (s, 1H), 8.20 (d, 1H), 8.06 (d, 1H), 8.01 (s, 1H), 7.93 (d, 1H), 7.65 (t, 1H), 7.64 (d, 2H), 7.55 (d, 1H), 7.03 (d, 2H), 6.50 (s, 1H), 5.20 (br, 1H), 3.89 (s, 3H), 3.07 (d, 3H); MS m/z [M+1] 452.06, 453.06, 454.07.

Example 27

6-(3-(3-aminophenyl)-6-(4-methoxyphenyl)-1H-indol-1-yl)-N-methylpyrimidin-4-amine

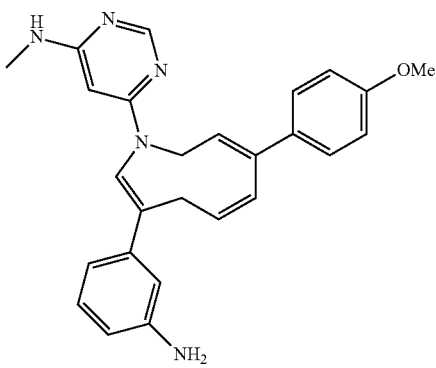 [SMILES: CNc1cc(N2/C=C(/c3cccc(N)c3)C/C=C\C(c3ccc(OC)cc3)=C/C2)ncn1]

Methanol/DMF (2:1, 20 mL) was added to 6-(6-(4-methoxyphenyl)-3-(3-nitrophenyl)-1H-indol-1-yl)-N-methylpyrimidin-4-amine (70 mg, 0.16 mmol) and Raney nickel (Raney Ni; about 50 mg). The mixture was stirred at room temperature for 12 hours under hydrogen gas (1 atm). The reaction solution was filtered using a diatomite pad and concentrated under reduced pressure. The target compound (60 mg) was obtained as brown solid.

MS m/z [M+1] 422.08, 423.09, 424.12.

Example 28

N-(3-(6-(4-methoxyphenyl)-1-(6-(methylamino)pyrimidin-4-yl)-1H-indol-3-yl)phenyl)acetamide

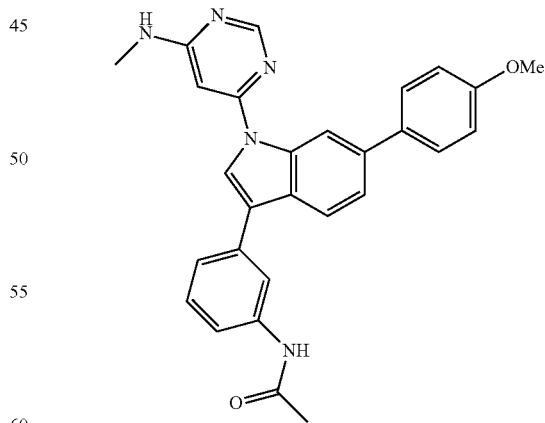

Acetic anhydride (20.3 µL, 0.214 mmol) was added to a mixture solution of 6-(3-(3-aminophenyl)-6-(4-methoxyphenyl)-1H-indol-1-yl)-N-methylpyrimidin-4-amine (30 mg, 0.071 mmol) and pyridine (28.7 µL, 0.355 mmol) in methyl ene chloride (2 mL) at room temperature. After stirring for 1 hour at room temperature, the reaction solution was added to saturated sodium bicarbonate aqueous solution and then extracted with ethyl acetate. The collected organic layer was washed with brine and concentrated under reduced pressure by drying with anhydrous magnesium sulfate. The residue was purified by chromatography (preparative HPLC). The target compound (15 mg) was obtained as white solid.

$^1$H NMR (400 MHz, CDCl$_3$) δ 8.61 (s, 1H0, 8.57 (s, 1H), 7.95 (d, 1H), 7.93 (d, 1H), 7.87 (s, 1H), 7.62 (d, 2H), 7.49 (d, 1H), 7.45 (m, 3H), 7.03 (d, 2H), 6.44 (s, 1H), 5.20 (br, 1H), 3.88 (s, 3H), 3.05 (d, 3H), 2.24 (s, 3H); MS m/z [M+1] 464.10, 465.10, 466.08.

Example 29 ethyl 4-(6-(4-methoxyphenyl)-1-(6-(methylamino) pyrimidin-4-yl)-1H-indol-3-yl)benzoate

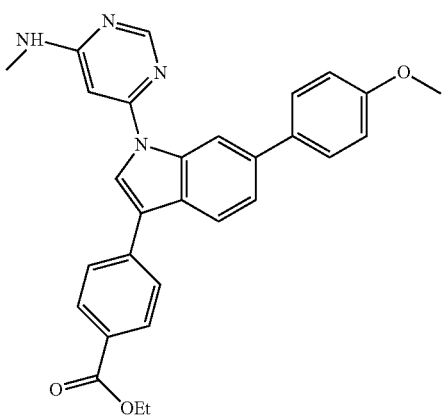

DMF (5 mL) was added to a mixture of 6-(3-bromo-6-(4-methoxyphenyl)-1H-indol-1-yl)-N-methylpyrimidin-4-amine (200 mg, 0.49 mmol), K$_3$PO$_4$ (312 mg, 0.885 mmol) and 4-(ethoxycarbonyl)phenylboronic acid (143 mg, 0.74 mmol) and then the dissolved gas was removed. After adding Pd(PPh$_3$)$_4$ (85 mg, 0.075 mmol), the mixture was stirred at 100° C. for 4 hours. After adding ethyl acetate and water and filtering using a diatomite pad, the organic layer was separated and the aqueous layer was extracted with ethyl acetate. The collected organic layer was washed with brine and concentrated under reduced pressure by drying with anhydrous magnesium sulfate. The residue was purified by chromatography (silica gel, EA:Hx=1:4-1:1). The target compound (70 mg) was obtained as white solid.

$^1$H NMR (400 MHz, CDCl$_3$) δ8.59 (s, 1H), 8.56 (s, 1H), 8.16 (d, 2H), 7.97 (s, 1H), 7.95 (d, 1H), 7.80 (d, 2H), 7.63 (d, 2H), 7.53 (d, 1H), 7.03 (d, 2H), 6.49 (s, 1H), 5.16 (br, 1H), 4.43 (q, 2H), 3.88 (s, 3H), 3.06 (d, 3H), 1.44 (t, 3H); MS m/z [M+1] 479.12, 480.07, 481.08.

Example 30

4-(6-(4-methoxyphenyl)-1-(6-(methylamino)pyrimidin-4-yl)-1H-indol-3-yl)benzoate

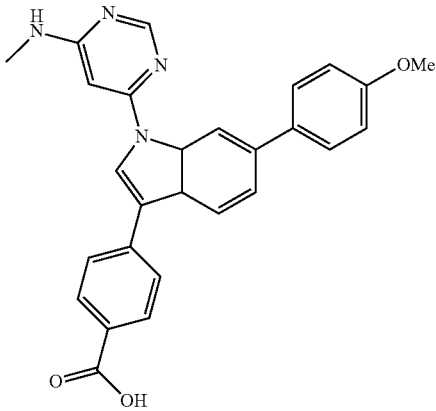 [SMILES: CNc1cc(N2C=C(c3ccc(C(=O)O)cc3)C3C=CC(c4ccc(OC)cc4)=CC32)ncn1]

1 M sodium hydroxide aqueous solution (5 mL) was added to a mixture solution of ethyl 4-(6-(4-methoxyphenyl)-1-(6-(methylamino)pyrimidin-4-yl)-1H-indol-3-yl)benzoate (70 mg, 0.146 mmol) in THF/methanol (1:1, 10 mL) at room temperature. After stirring for 12 hours at room temperature, the reaction solution was adjusted to pH 4 using 1 N hydrochloric acid aqueous solution. After adding water, the mixture was extracted with methylene chloride including a small amount of methanol. The collected organic layer was concentrated under reduced pressure by drying with anhydrous magnesium sulfate. The target compound was obtained as white solid.

$^1$H NMR (400 MHz, CDCl$_3$+MeOD) δ8.37 (s, 1H), 8.35 (s, 1H), 8.01 (d, 2H), 7.87 (s, 1H), 7.78 (d, 1H), 7.66 (d, 2H), 7.48 (d, 2H), 7.42 (d, 1H), 6.87 (d, 2H), 6.53 (br, 1H), 3.73 (s, 3H), 2.92 (s, 3H); MS m/z [M+1] 451.05, 452.06, 453.03.

Example 31

4-(6-(4-methoxyphenyl)-1-(6-(methylamino)pyrimidin-4-yl)-1H-indol-3-yl)-N-(2-morpholinoethyl)benzamide

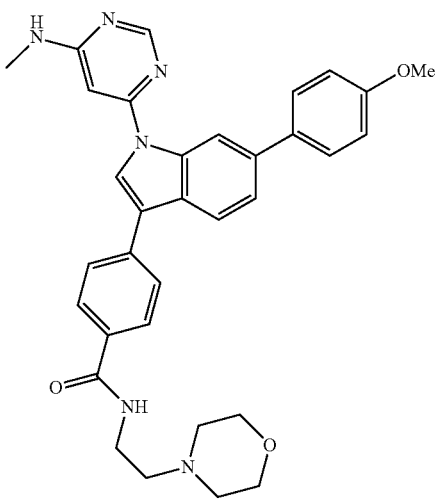 [SMILES: CNc1cc(-n2cc(-c3ccc(C(=O)NCCN4CCOCC4)cc3)c3ccc(-c4ccc(OC)cc4)cc32)ncn1]

O-(7-Azabenzotriazol-1-yl)-N,N,N,N-tetramethyluronium hexafluorophosphate (HATU; 63 mg, 0.167 mmol) was added to a mixture solution of 4-(6-(4-methoxyphenyl)-1-(6-(methylamino)pyrimidin-4-yl)-1H-indol-3-yl)benzoate (50 mg, 0.111 mmol), 2-morpholinoethanamine (14.6 μL, 0.111 mmol) and diisopropylethylamine (DIPEA; 29 μL, 0.167 mmol) in THF (2 mL) at room temperature. 2 hours later, the mixture was added to saturated sodium bicarbonate aqueous solution and then extracted with methylene chloride. The collected organic layer was washed with brine and concentrated under reduced pressure by drying with anhydrous magnesium sulfate. The residue was purified by chromatography (preparative HPLC). The target compound (15 mg) was obtained as white solid.

$^1$H NMR (400 MHz, CDCl$_3$+MeOD) δ 8.28 (br, 2H), 7.78 (s, 1H), 7.74 (d, 1H), 7.73 (d, 2H), 7.62 (d, 2H), 7.43 (d, 2H), 7.31 (d, 2H), 6.81 (d, 2H), 6.41 (br, 1H), 3.67 (s, 3H), 3.57 (m, 4H), 3.39 (t, 2H), 2.80 (s, 3H), 2.46 (t, 2H), 2.38 (m, 4H); MS m/z [M+1] 563.16, 564.13, 565.16.

Example 32

3-(4-methoxyphenyl)-1-(2-(methylthio)pyrimidin-4-yl)-6-(3-nitrophenyl)-1H-indole

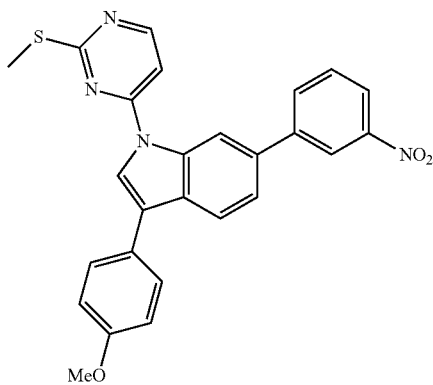 [SMILES: COc1ccc(-c2cn(-c3ccnc(SC)n3)c3cc(-c4cccc([N+](=O)[O-])c4)ccc23)cc1]

DMF (2 mL) was added to a mixture of 3-bromo-1-(2-(methylthio)pyrimidin-4-yl)-6-(3-nitrophenyl)-1H-indole (130 mg, 0.295 mmol), K$_3$PO$_4$ (188 mg, 0.885 mmol) and 4-methoxyphenylboronic acid (90 mg, 0.59 mmol) and then the dissolved gas was removed. After adding Pd(PPh$_3$)$_4$ (68 mg, 0.055 mmol), the mixture was stirred at 100° C. for 4 hours. After adding ethyl acetate and water and then filtering using a diatomite pad, the organic layer was separated and the aqueous layer was extracted with ethyl acetate. The collected organic layer was washed with brine and concentrated under reduced pressure by drying with anhydrous magnesium sulfate. The residue was purified by chromatography (silica gel, EA:Hx=1:4-1:1). The target compound (96 mg) was obtained as white solid.

MS m/z [M+1] 469.18.

Example 33

3-(4-methoxyphenyl)-1-(2-(methylsulfinyl)pyrimidin-4-yl)-6-(3-nitrophenyl)-1H-indole

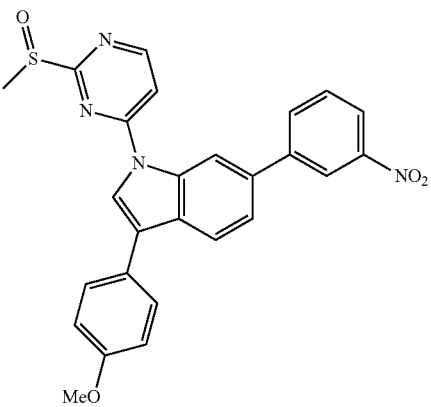 [SMILES: COc1ccc(-c2cn(-c3ccnc(S(C)=O)n3)c3cc(-c4cccc([N+](=O)[O-])c4)ccc23)cc1]

m-Chloroperoxybenzoic acid (m-CPBA; 70%, 95 mg, 0.384 mmol) was added to a mixture solution of 3-(4-methoxyphenyl)-1-(2-(methylthio)pyrimidin-4-yl)-6-(3-nitrophenyl)-1H-indole (90 mg, 0.192 mmol) in methylene chloride (10 mL) at 0° C. 2 hours later, after adding saturated sodium bicarbonate aqueous solution at 0° C., the mixture was extracted with ethyl acetate. The collected organic layer was washed with brine and concentrated under reduced pressure by drying with anhydrous magnesium sulfate. The target compound (90 mg) was obtained as white solid.

$^1$H NMR (400 MHz, CDCl$_3$) δ 9.37 (s, 1H), 8.82 (d, 1H), 8.61 (s, 1H), 8.21 (d, 1H), 7.95 (d, 1H), 7.79 (s, 1H), 7.68 (d, 1H), 7.67 (t, 1H), 7.64 (d, 2H), 7.45 (d, 1H), 7.08 (d, 2H), 6.79 (d, 1H), 3.91 (s, 3H), 3.08 (s, 3H); MS m/z [M+1] 485.25.

Example 34

4-(3-(4-methoxyphenyl)-6-(3-nitrophenyl)-1H-indol-1-yl)pyrimidin-2-amine

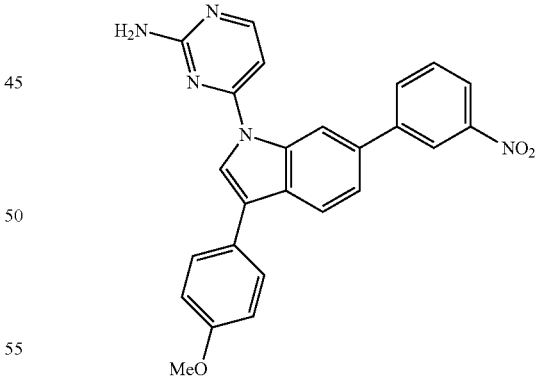

2.0 M ammonia isopropanol solution (2 mL) was added to 3-(4-methoxyphenyl)-1-(2-(methylsulfinyl)pyrimidin-4-yl)-6-(3-nitrophenyl)-1H-indole (90 mg) and then stirred at 100° C. for 3 hours in a sealed state. After cooling to room temperature, thus produced solid was filtered. After washing with isopropanol and then drying, the target compound (50 mg) was obtained as white solid.

$^1$H NMR (400 MHz, CDCl$_3$) δ8.82 (s, 1H), 8.57 (s, 1H), 8.37 (d, 1H0, 8.22 (d, 1H), 8.02 (d, 1H), 7.95 (d, 1H), 7.81 (s, 1H), 7.65 (t, 1H), 7.63 (d, 2H), 7.56 (d, 1H), 7.06 (d, 2H), 6.84 (d, 1H), 5.16 (s, 2H), 3.90 (s, 3H); MS m/z [M+1] 438.23.

Example 35

6-(3-(4-methoxyphenyl)-6-(3-nitrophenyl)-1H-indol-1-yl)-N-methylpyrimidin-4-amine

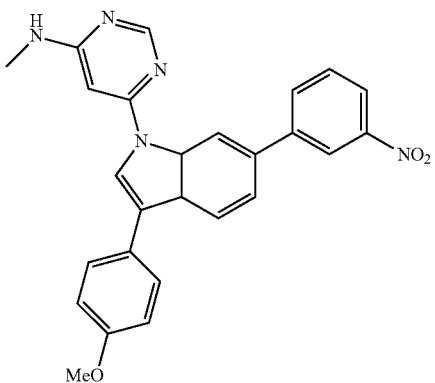 [SMILES: CNc1cc(N2C=C(c3ccc(OC)cc3)C3C=CC(c4cccc([N+](=O)[O-])c4)=CC32)ncn1]

DMF (5 mL) was added to a mixture of 6-(3-bromo-6-(3-nitrophenyl)-1H-indol-1-yl)-N-methylpyrimidin-4-amine (300 mg, 0.710 mmol), $K_3PO_4$ (452 mg, 2.13 mmol) and 4-methoxyphenylboronic acid (215 mg, 1.41 mmol) and then the dissolved gas was removed. After adding $Pd(PPh_3)_4$ (123 mg, 0.11 mmol), the mixture was stirred at 120° C. for 2 hours. After adding ethyl acetate and water and then filtering using a diatomite pad, the organic layer was separated and the aqueous layer was extracted with ethyl acetate. The collected organic layer was washed with brine and concentrated under reduced pressure by drying with anhydrous magnesium sulfate. The residue was purified by chromatography (silica gel, EA:Hx=1:4→1:1). The target compound was obtained as white solid.

$^1$H NMR (400 MHz, $CDCl_3$) δ 8.80 (s, 1H), 8.59 (s, 1H), 8.56 (m, 1H), 8.21 (d, 1H), 8.53 (d, 1H), 7.95 (d, 1H), 7.82 (s, 1H), 7.66 (d, 2H), 7.65 (t, 1H), 7.56 (d, 1H), 7.06 (d, 2H), 6.42 (s, 1H), 5.16 (br, 1H), 3.90 (s, 3H), 3.07 (d, 3H); MS m/z [M+1] 452.04, 453.04.

Example 36

6-(6-(3-aminophenyl)-3-(4-methoxyphenyl)-1H-indol-1-yl)-N-methylpyrimidin-4-amine

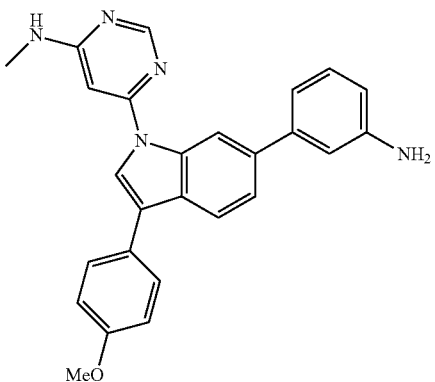 [SMILES: CNc1cc(-n2cc(-c3ccc(OC)cc3)c3ccc(-c4cccc(N)c4)cc32)ncn1]

Methanol/DMF (1:1, 20 mL) was added to 6-(3-(4-methoxyphenyl)-6-(3-nitrophenyl)-1H-indol-1-yl)-N-methylpyrimidin-4-amine (100 mg, 0.22 mmol) and Raney nickel (about 50 mg). The mixture was stirred at room temperature for 24 hours under hydrogen gas (1 atm). The reaction solution was filtered using a diatomite pad and then concentrated under reduced pressure. The target compound was obtained as brown solid.

$^1$H NMR (400 MHz, $CDCl_3$) δ8.60 (s, 1H), 7.91 (d, 1H), 7.82 (s, 1H), 7.69 (t, 1H), 7.66 (d, 2H), 7.49 (m, 3H), 7.09 (d, 1H), 7.04 (d, 2H), 6.45 (s, 1H), 5.10 (br, 1H), 3.88 (s, 3H), 3.05 (d, 3H); MS m/z [M+1] 422.11, 423.11.

Example 37

1-(4-chloro-3-(trifluoromethyl)phenyl)-3-(3-(3-(4-methoxyphenyl)-1-(6-(methylamino)pyrimidin-4-yl)-1H-indol-6-yl)phenyl)urea

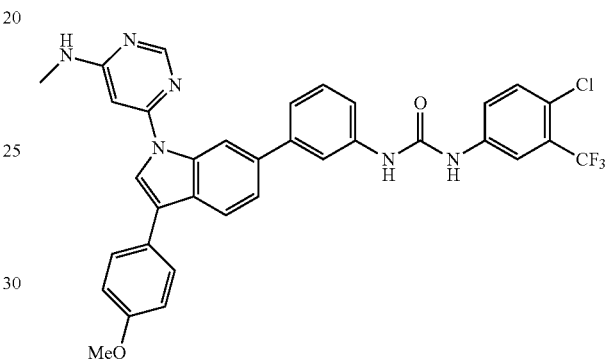

1-Chloro-4-isocyanato-2-(trifluoromethyl)benzene (15.8 mg, 0.071 mmol) was added to a mixture solution of 6-(6-(3-aminophenyl)-3-(4-methoxyphenyl)-1H-indol-1-yl)-N-methylpyrimidin-4-amine (20 mg, 0.047 mmol) in THF (1 mL) at room temperature. After stirring at room temperature for 12 hours, the reaction solution was concentrated under reduced pressure. The residue was purified by chromatography (silica gel, EA:Hx=1:1; DCM:MeOH=100:1; 20:1). The target compound was obtained as yellow solid.

MS m/z [M+1] 643.08, 645.01.

Example 38

1-(3,4-dichlorophenyl)-3-(3-(3-(4-methoxyphenyl)-1-(6-(methylamino)pyrimidin-4-yl)-1H-indol-6-yl)phenyl)urea

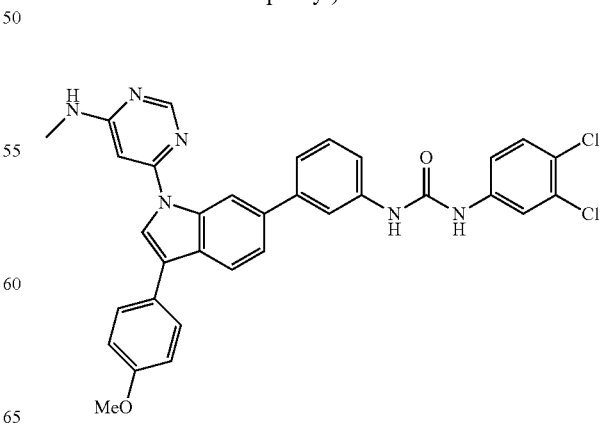

MS m/z [M+1] 608.91, 610.91.

Example 39

1-(2-methoxyphenyl)-3-(3-(3-(4-methoxyphenyl)-1-(6-(methylamino)pyrimidin-4-yl)-1H-indol-6-yl)phenyl)urea

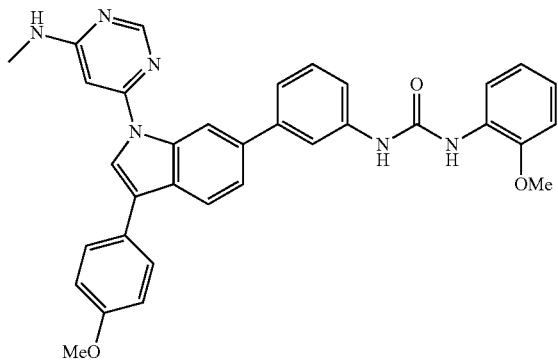 [SMILES: CNc1cc(-n2cc(-c3ccc(OC)cc3)c3ccc(-c4cccc(NC(=O)Nc5ccccc5OC)c4)cc32)ncn1]

MS m/z [M+1] 571.13, 572.09.

Example 40

1-(2-fluorophenyl)-3-(3-(3-(4-methoxyphenyl)-1-(6-(methylamino)pyrimidin-4-yl)-1H-indol-6-yl)phenyl)urea

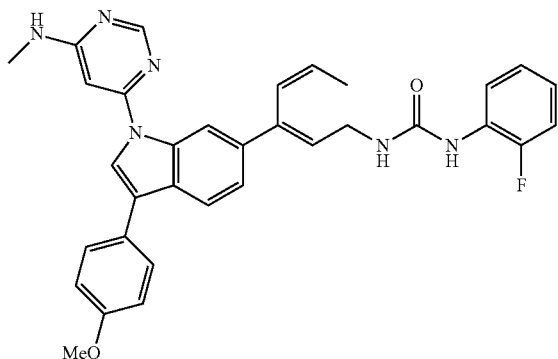 [SMILES: C/C=C\C(=C/CNC(=O)Nc1ccccc1F)c1ccc2c(-c3ccc(OC)cc3)cn(-c3cc(NC)ncn3)c2c1]

MS m/z [M+1] 559.09, 560.06.

Example 41

1-cyclohexyl-3-(3-(3-(4-methoxyphenyl)-1-(6-methylamino)pyrimidin-4-yl)-1H-indol-6-yl)phenyl)urea

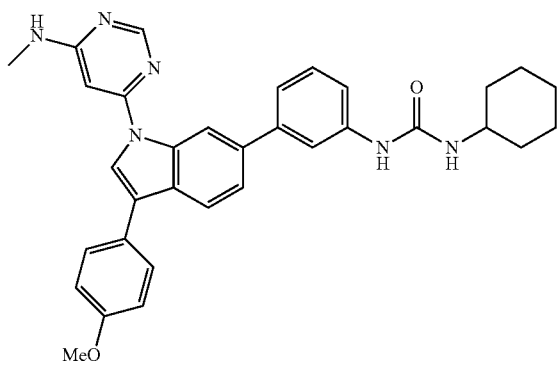 [SMILES: CNc1cc(-n2cc(-c3ccc(OC)cc3)c3ccc(-c4cccc(NC(=O)NC5CCCCC5)c4)cc32)ncn1]

MS m/z [M+1] 547.15, 548.13.

Example 42

N-(3-(3-(4-methoxyphenyl)-1-(6-(methylamino)pyrimidin-4-yl)-1H-indol-6-yl)phenyl)-3-morpholino-5-(trifluoromethyl)benzamide

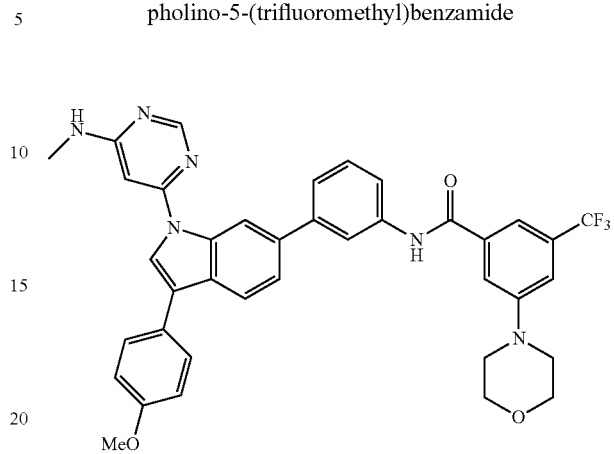

HATU (100 mg, 0.260 mmol) was added to a mixture solution of 3-morpholino-5-(trifluoromethyl)benzoate (54 mg, 0.195 mmol), 6-(6-(3-aminophenyl)-3-(4-methoxyphenyl)-1H-indol-1-yl)-N-methylpyrimidin-4-amine (55 mg, 0.130 mmol) and DIPEA (45 μL, 0.26 mmol) in THF (2 mL) at room temperature. 12 hours later, the mixture was added to saturated sodium bicarbonate aqueous solution and then extracted with methylene chloride. The collected organic layer was washed with brine and then concentrated under reduced pressure by drying with anhydrous magnesium sulfate. The residue was purified by chromatography (preparative HPLC). The target compound was obtained as yellow solid.

$^1$H NMR (400 MHz, DMSO-$d_6$) δ 10.47 (s, 1H), 8.50 (br, 1H), 8.08 (s, 1H), 7.95 (d, 1H), 7.83 (m, 1H), 7.75-7.69 (m, 5H), 7.55 (d, 2H), 7.52-7.48 (m, 2H), 7.40 (s, 1H), 7.09 (d, 2H), 6.80 (s, 1H), 3.82 (s, 3H), 3.77 (m, 4H), 3.30 (m, 4H), 2.90 (s, 3H); MS m/z [M+1] 679.08, 680.03, 681.10.

Example 43

N-(3-(3-(4-methoxyphenyl)-1-(6-(methylamino)pyrimidin-4-yl)-1H-indol-6-yl)phenyl)-4-methyl-3-nitrobenzamide

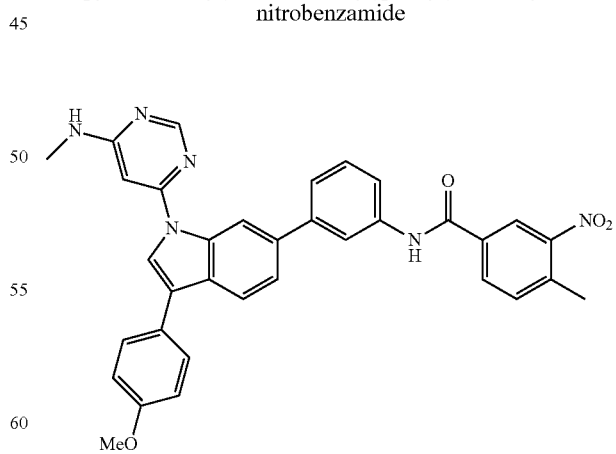

$^1$H NMR (400 MHz, DMSO-$d_6$) δ 10.58 (s, 1H), 8.61 (d, 1H), 8.48 (br, 1H), 8.24 (d, 1H), 8.09 (m, 1H), 7.95 (d, 1H), 7.88 (m, 1H), 7.76-7.73 (m, 3H), 7.55 (d, 1H), 7.52-7.44 (m, 4H), 7.09 (d, 2H), 6.78 (br, 1H), 3.96 (s, 3H), 2.90 (d, 3H), 2.66 (s, 3H); MS m/z [M+1] 585.05, 586.06, 587.06.

Example 44

N-(3-(3-(4-methoxyphenyl)-1-(6-(methylamino)pyrimidin-4-yl)-1H-indol-6-yl)phenyl)-3-(4-methyl-1H-imidazol-1-yl)-5-(trifluoromethyl)benzamide

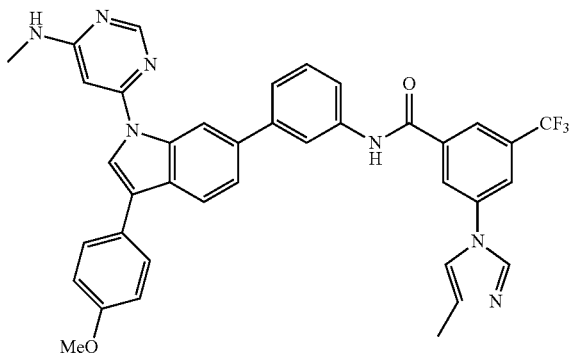 [SMILES: C/C=C/N(C=N)c1cc(C(=O)Nc2cccc(-c3ccc4c(-c5ccc(OC)cc5)cn(-c5cc(NC)ncn5)c4c3)c2)cc(C(F)(F)F)c1]

$^1$H NMR (400 MHz, DMSO-d$_6$) δ10.73 (s, 1H), 9.62 (br, 1H), 8.63 (s, 1H), 8.49-8.44 (m, 3H), 8.15 (s, 1H), 8.10 (m, 1H), 7.98 (d, 1H), 7.87 (m, 3H), 7.72 (d, 2H), 7.65-7.51 (m, 5H), 7.09 (d, 2H), 6.97 (d, 1H), 6.78 (br, 1H), 3.82 (s, 3H), 2.90 (d, 3H), 2.35 (s, 3H); MS m/z [M+1] 674.04, 675.05, 676.02.

Example 45

1-(4-chloro-3-(trifluoromethyl)phenyl)-3-(3-(6-(4-methoxyphenyl)-1-(6-(methylamino)pyrimidin-4-yl)-1H-indol-3-yl)phenyl)urea

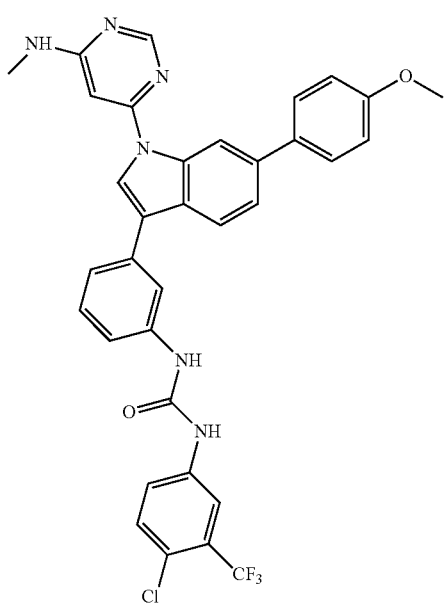

MS m/z [M+1] 643.12, 645.06.

Example 46

4-chloro-N-(3-(6-(4-methoxyphenyl)-1-(6-(methylamino)pyrimidin-4-yl)-1H-indol-3-yl)phenyl)-3-(trifluoromethyl)benzamide

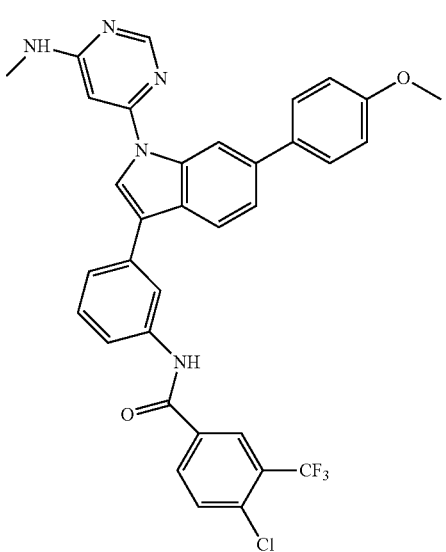

MS m/z [M+1] 628.07, 630.09.

Example 47

N-cyclopropyl-4-(6-(4-methoxyphenyl)-1-(6-(methylamino)pyrimidin-4-yl)-1H-indol-3-yl)benzamide

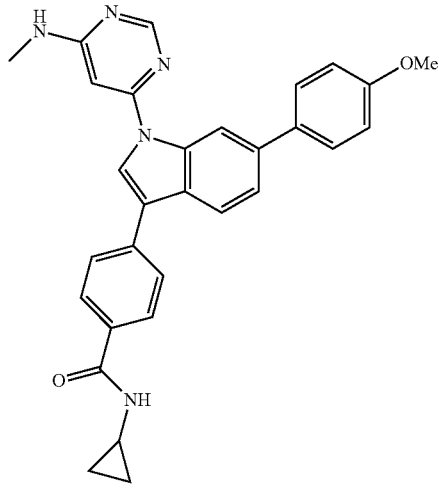 [SMILES: CNc1cc(-n2cc(-c3ccc(C(=O)NC4CC4)cc3)c3ccc(-c4ccc(OC)cc4)cc32)ncn1]

MS m/z [M+1] 490.01.

Example 48

1-(2,6-dimethylphenyl)-3-(3-(3-(4-methoxyphenyl)-1-(6-(methylamino)pyrimidin-4-yl)-1H-indol-6-yl)phenyl)urea

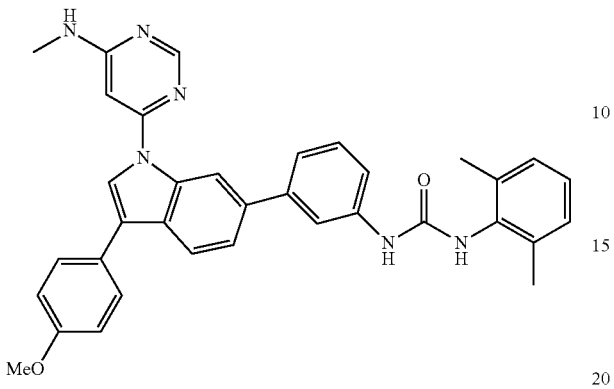

MS m/z [M+1] 569.34.

Example 49

1-(4-(4-ethylpiperazin-1-yl)-2-methoxyphenyl)-3-(3-(3-(4-methoxyphenyl)-1-(6-(methylamino)pyrimidin-4-yl)-1H-indol-6-yl)phenyl)urea

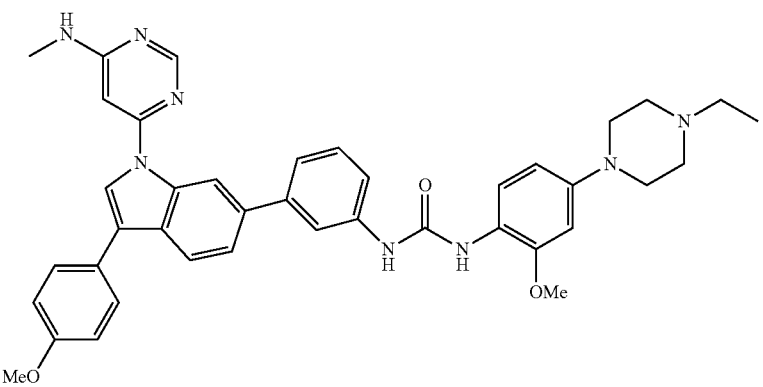 [SMILES: CCN1CCN(c2ccc(NC(=O)Nc3cccc(-c4ccc5c(-c6ccc(OC)cc6)cn(-c6cc(NC)ncn6)c5c4)c3)c(OC)c2)CC1]

MS m/z [M+1] 683.48.

Example 50

1-(5-chloro-2,4-dimethoxyphenyl)-3-(3-(3-(4-methoxyphenyl)-1-(6-(methylamino)pyrimidin-4-yl)-1H-indol-6-yl)phenyl)urea

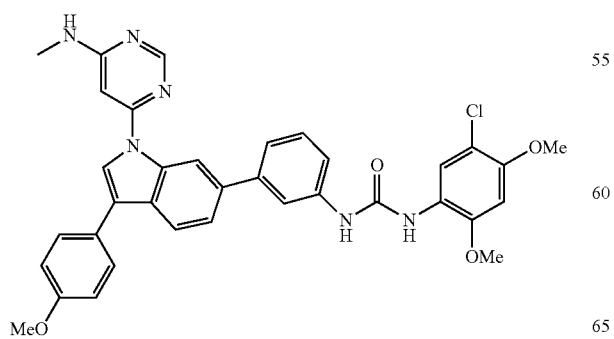

MS m/z [M+1] 635.36.

Example 51

N-(3-(6-(4-methoxyphenyl)-1-(6-(methylamino)pyrimidin-4-yl)-1H-indol-3-yl)phenyl)cyclopropanecarboxamide

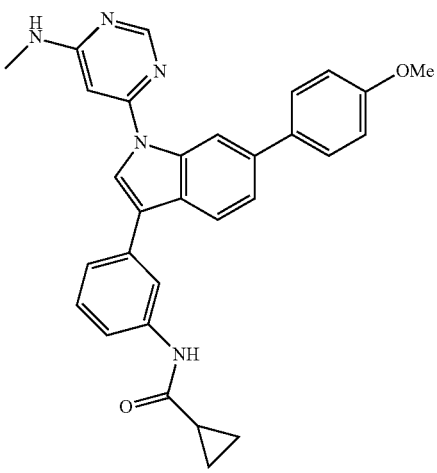 [SMILES: CNc1cc(-n2cc(-c3cccc(NC(=O)C4CC4)c3)c3ccc(-c4ccc(OC)cc4)cc32)ncn1]

MS m/z [M+1] 490.20.

Example 52

N-(3-(6-(4-methoxyphenyl)-1-(6-(methylamino)pyrimidin-4-yl)-1H-indol-3-yl)phenyl)cyclopropanesulfonamide

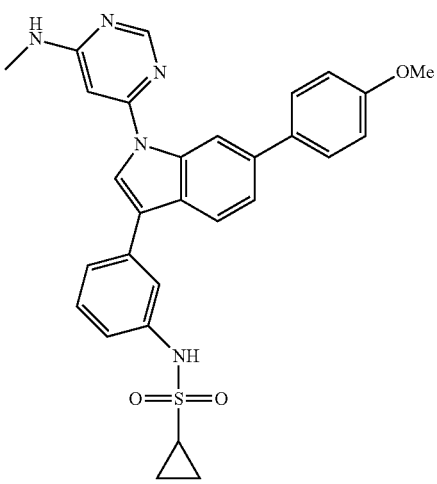 [SMILES: CNc1cc(-n2cc(-c3cccc(NS(=O)(=O)C4CC4)c3)c3ccc(-c4ccc(OC)cc4)cc32)ncn1]

6-(3-(3-Aminophenyl-6-(4-methoxyphenyl)-1H-indol-1-yl)-N-methylpyrimidin-4-amine (15 mg, 0.036 mmol) and triethylamine (99 μL, 0.712 mmol) were dissolved in tetrahydrofuran (1 mL). After adding cyclopropanesulfonyl chloride (54 μL, 0.534 mmol) at room temperature, the mixture was stirred at room temperature for 2 hours. The reaction solution was added to saturated sodium bicarbonate solution and then extracted with ethyl acetate. The organic layer was washed with brine and then concentrated under reduced pressure by drying with magnesium sulfate. The residue was purified by chromatography (silica gel, EtOAc:hexane=2:1→1:1). The target compound was obtained.

MS m/z [M+1] 526.13.

Example 53

6-(6-(4-methoxyphenyl)-1H,1'H-3,6'-biindol-1-yl)-N-methylpyrimidin-4-amine

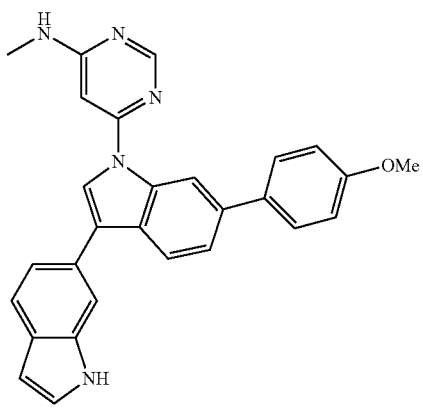 [SMILES: CNc1cc(-n2cc(-c3ccc4cc[nH]c4c3)c3ccc(-c4ccc(OC)cc4)cc32)ncn1]

6-(3-Bromo-6-(4-methoxyphenyl)-1H-indol-1-yl)-N-methylpyrimidin-4-amine (50 mg, 0.074 mmol), K₃PO₄ (47.1 mg, 0.222 mmol) and 6-(4,4,5,5-tetramethyl-1,3,2-dioxaborolan-2-yl)-1H-indole (27 mg, 0.111 mmol) were dissolved in dimethylformamide (2 mL) and then Pd(PPh₃)₄ (12.83 mg, 0.011 mmol) was added. After stirring at 120° C. for 3 hours, followed by addition of ethyl acetate and water, the reaction solution was filtered using a diatomite pad. The aqueous layer was extracted with ethyl acetate and the collected organic layer was washed with brine and then concentrated under reduced pressure by drying with magnesium sulfate. The residue was purified by chromatography (silica gel, EtOAc:hexane=1:10→1:4→1:2). The target compound was obtained as brown solid.

MS m/z [M+1] 446.13.

Example 54

6-(6-(4-methoxyphenyl)-3-(4-nitrophenyl)-1H-indol-1-yl)-N-methylpyrimidin-4-amine

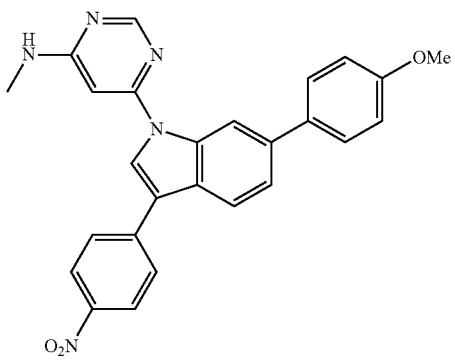 [SMILES: CNc1cc(-n2cc(-c3ccc([N+](=O)[O-])cc3)c3ccc(-c4ccc(OC)cc4)cc32)ncn1]

MS m/z [M+1] 452.06.

Example 55

6-(3-(4-aminophenyl)-6-(4-methoxyphenyl)-1H-indol-1-yl)-N-methylpyrimidin-4-amine

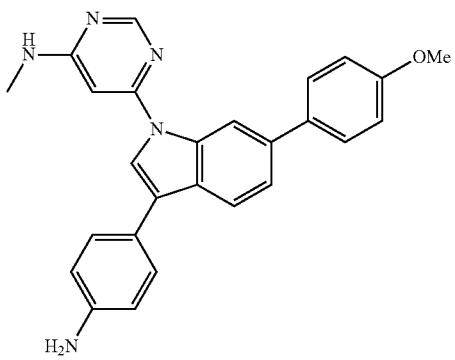

MS m/z [M+1] 422.13.

Example 56

6-(3-bromo-6-(4-methoxyphenyl)-1H-indol-1-yl)-N-(2-morpholinoethyl)pyrimidin-4-amine

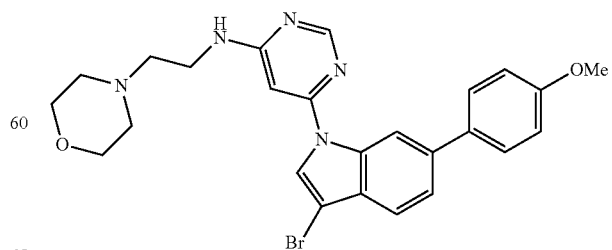

MS m/z [M+1] 507.90.

Example 57

6-(3-bromo-6-(4-methoxyphenyl)-1H-indol-1-yl)-N-cyclopropylpyrimidin-4-amine

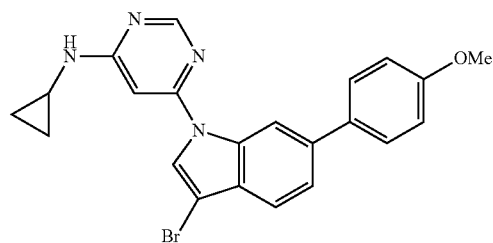 [SMILES: COc1ccc(-c2ccc3c(Br)cn(-c4cc(NC5CC5)ncn4)c3c2)cc1]

MS m/z [M+1] 434.82.

Example 58

6-(6-(4-methoxyphenyl)-3-(3-nitrophenyl)-1H-indol-1-yl)-N-(2-morpholinoethyl)pyrimidin-4-amine

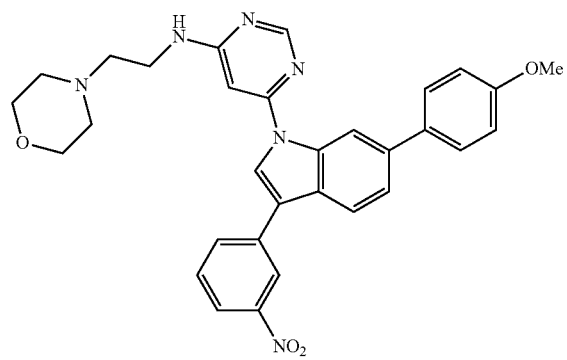

MS m/z [M+1] 550.96.

Example 59

N-cyclopropyl-6-(6-(4-methoxyphenyl)-3-(3-(nitrophenyl)-1H-indol-1-yl)pyrimidin-4-amine

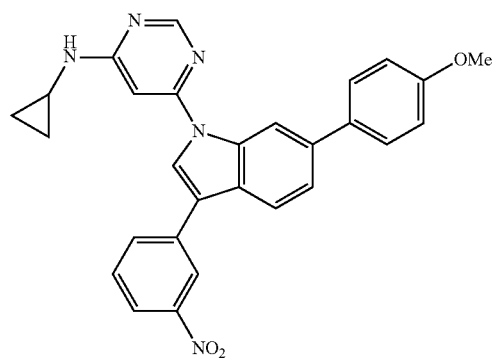 [SMILES: COc1ccc(-c2ccc3c(-c4cccc([N+](=O)[O-])c4)cn(-c4cc(NC5CC5)ncn4)c3c2)cc1]

MS m/z [M+1] 477.92.

Example 60

6-(3-(3-aminophenyl)-6-(4-methoxyphenyl)-1H-indol-1-yl)-N-(2-morpholinoethyl)pyrimidin-4-amine

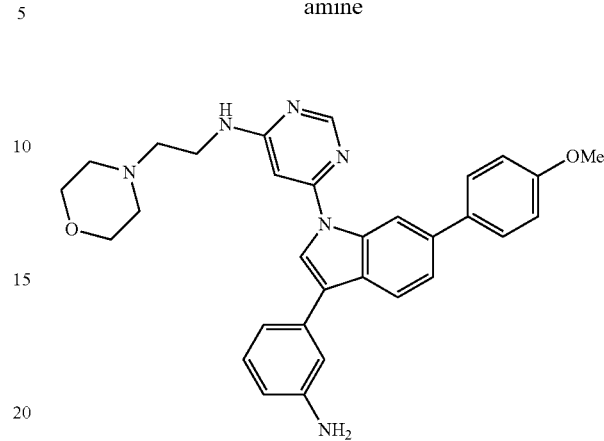

MS m/z [M+1] 521.01.

Example 61

6-(3-(3-aminophenyl)-6-(4-methoxyphenyl)-1H-indol-1-yl)-N-cyclopropylpyrimidin-4-amine

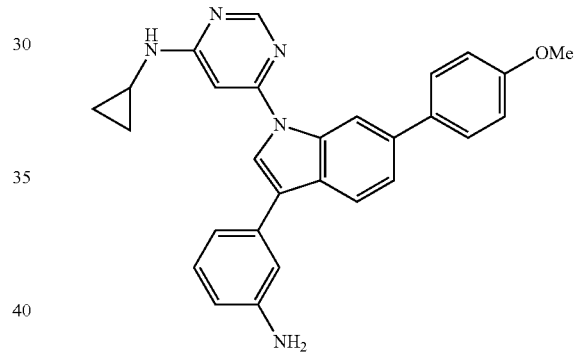

MS m/z [M+1] 448.00.

Example 62 ethyl 4-(6-(4-methoxyphenyl)-1-(6-(2-morpholinoethylamino)pyrimidin-4-yl)-1H-indol-3-yl)benzoate

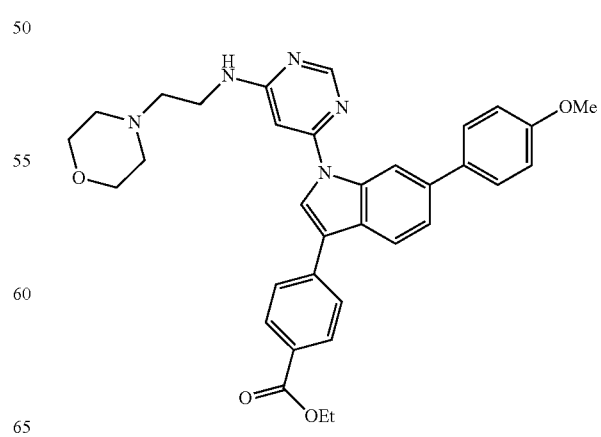

MS m/z [M+1] 578.00.

FORMULATION EXAMPLES

The novel compound represented by Chemical Formula 1 may be prepared into various formulations depending on purposes. The following examples illustrate some formulations comprising the compound represented by Chemical Formula 1 as an active ingredient, but they do not limit the present invention.

Formulation Example 1

Tablet (Direct Compression)

The active ingredient (5.0 mg) was sieved, mixed with lactose (14.1 mg), crospovidone USNF (0.8 mg) and magnesium stearate (0.1 mg), and then compressed into a tablet.

Formulation Example 2

Tablet (Wet Granulation)

The active ingredient (5.0 mg) was sieved and mixed with lactose (16.0 mg) and starch (4.0 mg). An adequate amount of the resulting solution was added to Polysorbate 80 (0.3 mg) dissolved in pure water, and then formed into granules. After drying, the granules were sieved and mixed with colloidal silicon dioxide (2.7 mg) and magnesium stearate (2.0 mg). The granules were compressed into a tablet.

Formulation Example 3

Powder and Capsule

The active ingredient (5.0 mg) was sieved and mixed with lactose (14.8 mg), polyvinylpyrrolidone (10.0 mg) and magnesium stearate (0.2 mg). The mixture was filled in a hard No. 5 gelatin capsule using an adequate apparatus.

Formulation Example 4

Injection

The active ingredient (100 mg) was mixed with mannitol (180 mg), $Na_2HPO_4 \cdot 12H_2O$ (26 mg) and distilled water (2974 mg) to prepare an injection.

TEST EXAMPLES

Test Example 1

Measurement of B-Raf Kinase Activity (Kinase Cascade Assay)

(1) Activation of MAP Kinase 2/Erk2 by B-Raf

Magnesium/ATP solution (500 µM ATP, 75 mM magnesium chloride) was prepared (10 µL). Diluted B-Raf-V600E enzyme (2.5 µL) was added at a final concentration of 1 ng/mL. and inactivated MEK1 (1.6 µL) was added at a final concentration of 0.4 µg/mL. Then, inactivated MAP Kinase 2/Erk2 (4 µL) was added at a final concentration of 1.0 µg/mL. The test compound was prepared at a concentration of 10 mM in dimethylsulfoxide (DMSO) and diluted to various concentrations (DMSO 2.6%). The final volume was adjusted to 38 µL by adding Assay Dilution Butter I (ADBI) and the mixture was allowed to react at 30° C. for 30 minutes. 5 µL of the mixture solution was taken to perform the next process.

(2) Phosphorylation of Myelin Basic Protein (MBP)

The mixture solution (5 µL) was treated with assay dilution buffer (10 µL) and then with myelin basic protein (MBP, 2 mg/mL, 10 µL). [γ-32P] ATP (100 µCi/container) diluted to 1/10 was added in 10 µL aliquots. After reaction at 30° C. for 2 10 minutes and then placing P81 paper in a scintillation vial, spotting was performed slowly using 25 µL of the reaction mixture. After washing 4 times with 0.75% phosphoric acid for 10 minutes and washing once with acetone for 5 minutes, 5 mL of scintillation cocktail was added to the scintillation vial. Signals were recorded using a scintillation counter.

The B-Raf kinase inhibitory activity of some compounds represented by Chemical Formula 1 is given in Table 1. $IC_{50}$ ranged from 0.12 to 20 µM.

TABLE 1

| Test compounds | B-Raf-V600E kinase inhibitory activity ($IC_{50}$, µM) |
|---|---|
| Example 25 | <10 |
| Example 27 | <10 |
| Example 30 | <10 |
| Example 39 | <10 |

Test Example 2

Measurement of Inhibitory Activity Against Proliferation of A375P Melanoma Cells A375P cells purchased from ATCC were cultured in DMEM [10% FBS, 1% penicillin/streptomycin] at 37° C. in the presence of 5% $CO_2$. The cultured A375P cells were harvested with 0.05% trypsin-0.02% EDTA and seeded in a 96-well plate at $5 \times 10^3$ cells per well.

3-(4,5-Dimethylthiazol-2-yl)-2,5-diphenyltetrazolium bromide (MTT) assay (CellTiter 96 Assay, Promega) was employed to measure cell viability. After adding 15 µL of a dye per well and culturing for 2 hours, the cells were treated with 100 µL of a stop solution and absorbance was measured 24 hours later. The test compound was treated a day after plating. The test compound had been sequentially diluted at 12 concentrations from a 10 mM stock solution using sterilized dimethylsulfoxide (DMSO) and treated with an amount of 0.5 µL. Absorbance at 590 nm was recorded using EnVision2103, and $GI_{50}$ value was calculated using GraphPad Prism 4.0 software.

The compounds represented by Chemical Formula 1 exhibited inhibitory activity against proliferation of the A375P human melanoma cells with the B-Raf-V600E mutants overexpressed. $GI_{50}$ ranged from 0.001 to 10 µM. The inhibitory activity against proliferation of the A375P cells of some typical compounds according to the present invention is given in Table 2.

TABLE 2

| Test compounds | Inhibitory activity against proliferation of A375P cells ($GI_{50}$, µM) |
|---|---|
| Example 9 | <10 |
| Example 13 | <10 |
| Example 14 | <10 |
| Example 26 | <10 |
| Example 27 | <10 |
| Example 28 | <10 |
| Example 30 | <10 |
| Example 31 | <10 |

TABLE 2-continued

| Test compounds | Inhibitory activity against proliferation of A375P cells (GI$_{50}$, μM) |
|---|---|
| Example 33 | <10 |
| Example 37 | <10 |
| Example 39 | <10 |
| Example 45 | <10 |

As described, since the 1,3,6-substituted indole compound represented by Chemical Formula 1 or a pharmaceutically acceptable thereof exhibits inhibitory activity for protein kinases, it is useful for preventing and treating diseases caused by abnormal cell growth induced by protein kinases, such as cancers selected from the group consisting of stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma and fibroadenoma.

While the present invention has been described with respect to the specific embodiments, it will be apparent to those skilled in the art that various changes and modifications may be made without departing from the spirit and scope of the invention as defined in the following claims.

What is claimed is:

1. A method of inhibiting a Raf protein kinase comprising contacting a cell with a pharmaceutical composition comprising an active ingredient that is a 1,3,6-substituted indole compound represented by chemical formula 1, or a pharmaceutically acceptable salt thereof:

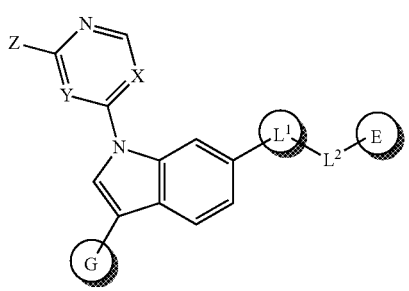

(1)

wherein

X and Y are independently selected from N or CH;

Z is selected from the group consisting of hydrogen; halogen; linear, branched or cyclic saturated or unsaturated $C_1$-$C_6$ alkyl; cyano; $OR^1$; —$SR^1$; $NHR^1$; —C(O)$NHR^1$; —NHC(O)$R^1$; —NHC(O)$NHR^1$; —S(O)$R^1$; and —S(O)$_2R^1$;

G is selected from the group consisting of halogen; 5- to 7-membered substituted or unsubstituted aryl; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

L1 is selected from the group consisting of 5- to 7-membered substituted or unsubstituted aryl; biaryl resulting from two fused 5- to 7-membered substituted or unsubstituted aryls; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

L2 is nonexistent or selected from the group consisting of —$NR^2C(O)$—; —C(O)$NR^2$—; —$NR^2C(O)NR^3$—; —S(O)$NR^2$—; and —S(O)$_2NR^2$—;

E is selected from the group consisting of hydrogen; linear, branched or cyclic saturated or unsaturated $C_1$-$C_6$ alkyl; —$NO_2$; —$OR^3$; —$NR^3R^4$; —NHC(O)$R^3$; —C(O)$OR^3$; 5- to 7-membered substituted or unsubstituted aryl; biaryl resulting from two fused 5- to 7-membered substituted or unsubstituted aryls; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

$R^1$ is selected from the group consisting of hydrogen; linear, branched or cyclic saturated or unsaturated $C_1$-$C_6$ alkyl; saturated or unsaturated $C_1$-$C_6$ alkyl substituted with heteroaryl or heterocyclic ring selected from the group consisting of pyrrolidinonyl, pyrrolidinyl, piperidinyl, piperazinyl, morpholinyl and aziridinyl;

$R^2$, $R^3$ and $R^4$ are independently selected from the group consisting of hydrogen; and linear, branched or cyclic saturated or unsaturated $C_1$-$C_6$ alkyl;

wherein the above aryl, heteroaryl, biaryl or heterocyclic is independently substituted or unsubstituted with 1 to 3 substituent(s) selected from the group consisting of hydrogen; halogen; linear, branched or cyclic saturated or unsaturated $C_1$-$C_6$ alkyl; $C_1$-$C_6$ haloalkyl containing 1 to 10 halogen atoms; cyano; —$NO_2$; —OBoc; —$OR^5$; —O(CH$_2$)$_n$$NR^6R^7$ (where n is an integer from 1 to 6); —$NR^6R^7$; —$NR^5COR^6$; —$NR^5C(O)NR^6R^7$; —C(O)$R^6$; —C(O)$OR^6$; —C(O)$NR^6R^7$; —C(O)NH(CH$_2$)$_n$$NR^6R^7$; —S(O)$R^6$; —S(O)$_2R^6$; —S(O)$_2NR^6R^7$; 5- to 7-membered aryl; biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; and $R^5$, $R^6$ and $R^7$ are independently selected from the group consisting of hydrogen; halogen; linear, branched or cyclic saturated or unsaturated $C_1$-$C_6$ alkyl; 5- to 7-membered aryl; biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; or $NR^6R^7$ forms a 5- to 7-membered heteroaryl or a heterocyclic ring by further including 1 to 3 other heteroatom(s); wherein the aryl, biaryl, heteroaryl or heterocyclic ring may be substituted with 1 to 3 substituent(s) selected from the group consisting of halogen, $C_1$-$C_6$ alkyl, and $C_1$-$C_6$ haloalkyl containing 1 to 10 halogen atom(s).

2. A method of treating cancers selected from the group consisting of stomach cancer, non-small cell lung cancer, liver cancer, colorectal cancer, small intestine cancer, pancreatic cancer, brain cancer metastasized from breast cancer, bone cancer, melanoma, breast cancer, sclerosing adenoma, ovarian cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, non-Hodgkin's lymphoma and fibroadenoma, the method comprising administering, to a patient in need thereof, a pharmaceutical composition comprising an active ingredient that is a 1,3,6-substituted indole compound represented by Chemical Formula 1, or a pharmaceutically acceptable salt thereof:

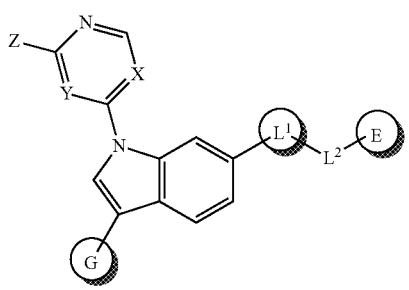

(1)

wherein

X and Y are independently selected from N or CH;

Z is selected from the group consisting of hydrogen; halogen; linear, branched or cyclic saturated or unsaturated $C_1$-$C_6$ alkyl; cyano; $OR^1$; —$SR^1$; $NHR^1$; —C(O)$NHR^1$; —NHC(O)$R^1$; —NHC(O)$NHR^1$; —S(O)$R^1$; and —S(O)$_2R^1$;

G is selected from the group consisting of halogen; 5- to 7-membered substituted or unsubstituted aryl; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

L1 is selected from the group consisting of 5- to 7-membered substituted or unsubstituted aryl; biaryl resulting from two fused 5- to 7-membered substituted or unsubstituted aryls; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

L2 is nonexistent or selected from the group consisting of —$NR^2C(O)$—; —C(O)$NR^2$—; —$NR^2C(O)NR^3$—; —S(O)$NR^2$—; and —S(O)$_2NR^2$—;

E is selected from the group consisting of hydrogen; linear, branched or cyclic saturated or unsaturated $C_1$-$C_6$ alkyl; —$NO_2$; —$OR^3$; —$NR^3R^4$; —NHC(O)$R^3$; —C(O)$OR^3$; 5- to 7-membered substituted or unsubstituted aryl; biaryl resulting from two fused 5- to 7-membered substituted or unsubstituted aryls; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

$R^1$ is selected from the group consisting of hydrogen; linear, branched or cyclic saturated or unsaturated $C_1$-$C_6$ alkyl; saturated or unsaturated $C_1$-$C_6$ alkyl substituted with heteroaryl or heterocyclic ring selected from the group consisting of pyrrolidinonyl, pyrrolidinyl, piperidinyl, piperazinyl, morpholinyl and aziridinyl;

$R^2$, $R^3$ and $R^4$ are independently selected from the group consisting of hydrogen; and linear, branched or cyclic saturated or unsaturated $C_1$-$C_6$ alkyl;

wherein the above aryl, heteroaryl, biaryl or heterocyclic is independently substituted or unsubstituted with 1 to 3 substituent(s) selected from the group consisting of hydrogen; halogen; linear, branched or cyclic saturated or unsaturated $C_1$-$C_6$ alkyl; $C_1$-$C_6$ haloalkyl containing 1 to 10 halogen atoms; cyano; —$NO_2$; —OBoc; —$OR^5$; —O(CH$_2$)$_n$$NR^6R^7$ (where n is an integer from 1 to 6 ); —$NR^6R^7$; —$NR^5COR^6$; —$NR^5C(O)NR^6R^7$; —C(O)$R^6$; —C(O)$OR^6$; —C(O)$NR^6R^7$; —C(O)NH(CH$_2$)$_n$$NR^6R^7$; —S(O)$R^6$; —S(O)$_2R^6$; —S(O)$_2NR^6R^7$; 5- to 7-membered aryl; biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; and $R^5$, $R^6$ and $R^7$ are independently selected from the group consisting of hydrogen; halogen; linear, branched or cyclic saturated or unsaturated $C_1$-$C_6$ alkyl; 5- to 7-membered aryl; biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; or $NR^6R^7$ forms a 5- to 7-membered heteroaryl or a heterocyclic ring by further including 1 to 3 other heteroatom(s); wherein the aryl, biaryl, heteroaryl or heterocyclic ring may be substituted with 1 to 3 substituent(s) selected from the group consisting of halogen, $C_1$-$C_6$ alkyl, and $C_1$-$C_6$ haloalkyl containing 1 to 10 halogen atom(s).

3. A method of treating melanoma, the method comprising administering, to a patient in need thereof, a pharmaceutical composition comprising an active ingredient that is a 1,3,6-substituted indole compound represented by Chemical Formula 1, or a pharmaceutically acceptable salt thereof:

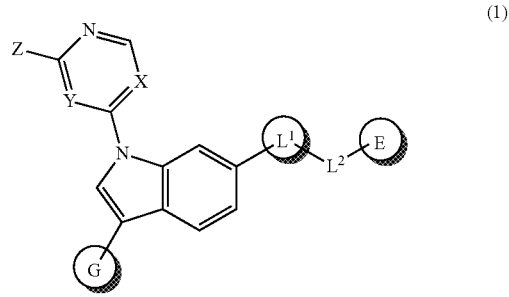

(1)

wherein

X and Y are independently selected from N or CH;

Z is selected from the group consisting of hydrogen; halogen; linear, branched or cyclic saturated or unsaturated $C_1$-$C_6$ alkyl; cyano; OR —$SR^1$;$NHR^1$; —C(O)$NHR^1$; —NHC(O)$R^1$; —NHC(O)$NHR^1$; —S(O)$R^1$; and —S(O)$_2R^1$;

G is selected from the group consisting of halogen; 5- to 7-membered substituted or unsubstituted aryl; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

L1 is selected from the group consisting of 5- to 7-membered substituted or unsubstituted aryl; biaryl resulting from two fused 5- to 7-membered substituted or unsubstituted aryls; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

L2 is nonexistent or selected from the group consisting of —$NR^2C(O)$—; —$C(O)NR^2$—; —$NR^2C(O)NR^3$—; —$S(O)NR^2$—; and —$S(O)_2NR^2$—;

E is selected from the group consisting of hydrogen; linear, branched or cyclic saturated or unsaturated $C_1$-$C_6$ alkyl; —$NO_2$; —$OR^3$; —$NR^3R^4$; —$NHC(O)R^3$; —$C(O)OR^3$; 5- to 7-membered substituted or unsubstituted aryl; biaryl resulting from two fused 5- to 7-membered substituted or unsubstituted aryls; 5- to 7-membered substituted or unsubstituted heteroaryl containing 1 to 3 heteroatom(s) selected from nitrogen, oxygen and sulfur; and a 5- to 7-membered substituted or unsubstituted heterocyclic group containing 1 to 3 heteroatom(s) selected from nitrogen, oxygen and sulfur;

$R^1$ is selected from the group consisting of hydrogen; linear, branched or cyclic saturated or unsaturated $C_1$-$C_6$ alkyl; saturated or unsaturated $C_1$-$C_6$ alkyl substituted with heteroaryl or heterocyclic ring selected from the group consisting of pyrrolidinonyl, pyrrolidinyl, piperidinyl, piperazinyl, morpholinyl and aziridinyl;

$R^2$, $R^3$ and $R^4$ are independently selected from the group consisting of hydrogen; and linear, branched or cyclic saturated or unsaturated $C_1$-$C_6$ alkyl;

wherein the above aryl, heteroaryl, biaryl or heterocyclic is independently substituted or unsubstituted with 1 to 3 substituent(s) selected from the group consisting of hydrogen; halogen; linear, branched or cyclic saturated or unsaturated $C_1$-$C_6$ alkyl; $C_1$-$C_6$ haloalkyl containing 1 to 10 halogen atoms; cyano; —$NO_2$; —OBoc; —$OR^5$; —$O(CH_2)_nNR^6R^7$ (where n is an integer from 1 to 6); —$NR^6R^7$; —$NR^5COR^6$; —$NR^5C(O)NR^6R^7$; —$C(O)R^6$; —$C(O)OR^6$; —$C(O)NR^6R^7$; —$C(O)NH(CH_2)_nNR^6R^7$; —$S(O)R^6$; —$S(O)_2R^6$; —$S(O)_2NR^6R^7$; 5- to 7-membered aryl; biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; and $R^5$, $R^6$ and $R^7$ are independently selected from the group consisting of hydrogen; halogen; linear, branched or cyclic saturated or unsaturated $C_1$-$C_6$ alkyl; 5- to 7-membered aryl; biaryl resulting from two fused 5- to 7-membered aryls; 5- to 7-membered heteroaryl containing 1 to 3 heteroatom(s) selected from nitrogen, oxygen and sulfur; and a 5- to 7-membered heterocyclic ring containing 1 to 3 heteroatom(s) selected from nitrogen, oxygen and sulfur; or $NR^6R^7$ forms a 5- to 7-membered heteroaryl or a heterocyclic ring by further including 1 to 3 other heteroatom(s); wherein the aryl, biaryl, heteroaryl or heterocyclic ring may be substituted with 1 to 3 substituent(s) selected from the group consisting of halogen, $C_1$-$C_6$ alkyl, and $C_1$-$C_6$ haloalkyl containing 1 to 10 halogen atom(s).

\* \* \* \* \*